United States Patent
Hipfel et al.

(10) Patent No.: US 10,705,089 B2
(45) Date of Patent: Jul. 7, 2020

(54) METHODS AND KITS FOR THE DIAGNOSIS OF CANCER

(71) Applicants: BioNTech Diagnostics GmbH, Mainz (DE); TRON-Translationale Onkologie An der Universitatsmedizin der Johannes Gutenberg-Universitat Mainz Gemein-Nutzige GmbH, Mainz (DE)

(72) Inventors: Rainer Hipfel, Wiesbaden (DE); Clara Werner, Mainz (DE); Andree Rothermel, Rimbach (DE); Ugur Sahin, Mainz (DE); Yvonne Kuhne, Langen (DE)

(73) Assignees: BioNTech Disgnostics GmbH, Mainz (DE); TRON-Translationale Onkologie an der Universitätsmedizin der Johannes Gutenberg-Universität Mainz gemeinnützige GmbH, Mainz (DE)

( * ) Notice: Subject to any disclaimer, the term of this patent is extended or adjusted under 35 U.S.C. 154(b) by 71 days.

(21) Appl. No.: 15/309,966

(22) PCT Filed: Apr. 15, 2015

(86) PCT No.: PCT/EP2015/058179
§ 371 (c)(1),
(2) Date: Nov. 9, 2016

(87) PCT Pub. No.: WO2015/172960
PCT Pub. Date: Nov. 19, 2015

(65) Prior Publication Data
US 2019/0033316 A1    Jan. 31, 2019

(30) Foreign Application Priority Data

May 16, 2014 (EP) .................. PCT/EP2014/060096

(51) Int. Cl.
*G01N 33/574* (2006.01)
*G01N 33/564* (2006.01)

(52) U.S. Cl.
CPC ..... *G01N 33/57488* (2013.01); *G01N 33/564* (2013.01); *G01N 33/57407* (2013.01); *G01N 33/57423* (2013.01); *G01N 2800/52* (2013.01); *G01N 2800/60* (2013.01)

(58) Field of Classification Search
None
See application file for complete search history.

(56) References Cited

U.S. PATENT DOCUMENTS

2009/0075832 A1    3/2009   Neuman et al.
2010/0204055 A1    8/2010   Bonner-Ferraby et al.

FOREIGN PATENT DOCUMENTS

WO    WO 2009040782 A2 *    4/2009
WO    WO-2011/025542 A1    3/2011

OTHER PUBLICATIONS

Farlow et al. Development of a multiplexed tumor-associated autoantibody-based blood test for the detection of non-small cell lung cancer. Clin. Cancer Res. 16(13): 3452-3462, Published Online Jun. 22, 2010.*
Shan et al. Cancer Letters 328(1): Supplemental Table 1, pp. 1-4, 2013.*
Brower V, "Biomarker studies abound for early detection of lung cancer," J Nat'l Cancer Inst. 2009; 101:11-3.
Chapman, et al., "Autoantibodies in lung cancer: possibilities for early detection and subsequent cure," Thorax. 2008; 63:228-33.
Chapman, et al., "EarlyCDT®-Lung test: improved clinical utility through additional autoantibody assays," Tumour Biol. Oct. 2012; 33(5):1319-26.
Cuzick J, et al., "Management of women who test positive for high-risk types of human papillomavirus: the HART study," Lancet. Dec. 6, 2003; 362(9399):1871-1876.
Goulart BH, et al., "Lung cancer screening with low-dose computed tomography: costs, national expenditures, and cost-effectiveness," J Natl Compr Canc Netw. Feb. 2012; 10(2):267-75.
Harper DM., "Predictive Values: What Do They Tell Us?" Trends in Cervical Health. www.cervicalhealth.com. vol. 4; Winter 2007 (4 pages).
Pereira-Faca SR, et al., "Identification of 14-3-3 theta as an antigen that induces a humoral response in lung cancer," Cancer Res. 2007; 67:12000-6.
Qiu J, Choi G, et al., "Occurrence of autoantibodies to annexin I, 14-3-3 theta and LAMR1 in prediagnostic lung cancer sera," J Clin Oncol. 2008; 26:5060-6.
Renard, et al., "rapmad: Robust analysis of peptide microarray data," BMC Bioinformatics, vol. 12., No. 1, 10 pages, (2011).
Shan, et al., "A cancer/testis antigen microarray to screen autoantibody biomarkers of non-small cell lung cancer," Cancer Lett. Jan. 1, 2013; 328(1):160-7.
Solassol J, et al., "Autoantibodies against tumor-related antigens: new tools for early detection of lung cancer," Bull Cancer Dec. 2011; 98(12):1419-30 (Original in French // Abstract—1 page).
Tan, et al., "Serum autoantibodies as biomarkers for early cancer detection," FEBS J., vol. 276, No. 23, pp. 6880-6904 (2009).
The National Lung Screening Trial Research Team. Reduced Lung-Cancer Mortality with Low-Dose Computed Tomographic Screening. N Engl J Med 2011; 365:395-409 Aug. 4, 2011.
Yang, et al., "Identification of tumor antigens in human lung squamous carcinoma by serological proteome analysis," J Proteome Res. 2007; 6:751-8.
Zaenker P, Ziman MR, "Serologic autoantibodies as diagnostic cancer biomarkers—a review," Cancer Epidemiol Biomarkers Prev. Dec. 2013; 22(12):2161-81.
Zhang C, et al., "Autoantibodies against p16 protein-derived peptides may be a potential biomarker for non-small cell lung cancer," Tumour Biol. Oct. 13, 2013.

(Continued)

Primary Examiner — Alana Harris Dent
(74) Attorney, Agent, or Firm — Ballard Spahr LLP

(57) ABSTRACT

The present invention relates to methods and kits for the diagnosis, prognosis and/or monitoring of cancer in a patient. The present invention further relates to isolated peptides, panels of isolated peptides and diagnostic devices.

26 Claims, 8 Drawing Sheets

Specification includes a Sequence Listing.

(56) References Cited

OTHER PUBLICATIONS

International Search Report dated Jul. 3, 2015 for application PCT/EP2015/058179, filed on Apr. 15, 2015 and published as WO 2015/172960 on Nov. 19, 2015 (Applicant—Biontech Diagnostics, GmbH // Inventor—Hipfel, et al.) (5 pages).
Written Opinion dated Jul. 3, 2015 for application PCT/EP2015/058179, filed on Apr. 15, 2015 and published as WO 2015/172960 on Nov. 19, 2015 (Applicant—Biontech Diagnostics, GmbH // Inventor—Hipfel, et al.) (7 pages).
International Preliminary Report on Patentability dated Nov. 22, 2016 for application PCT/EP2015/058179, filed on Apr. 15, 2015 and published as WO 2015/172960 on Nov. 19, 2015 (Applicant—Biontech Diagnostics, GmbH // Inventor—Hipfel, et al.) (8 pages).

\* cited by examiner

Figure 7

| | 1 | 2 | 3 | 4 | 5 | 6 | 7 | 8 | 9 | 10 | 11 | 12 |
|---|---|---|---|---|---|---|---|---|---|---|---|---|
| Peptide-Mix 1 (NY-ESO-1) n=3 | | | | | | | | | | | | |
| Peptide-Mix 2 (NY-ESO-1) n=4 | | | | | | | | | | | | |
| Peptide-Mix 3 (NY-ESO-1) n=3 | | | | | | | | | | | | |
| Peptide-Mix 4 (p53) n=4 | | | | | | | | | | | | |
| Peptide-Mix 5 (MAGE-A1/A3/A4) n=3 | | | | | | | | | | | | |
| Peptide-Mix 6 (XAGE-1 Endoplasmin TRIO K-ras 2) n=4 | | | | | | | | | | | | |
| Blank for normalization (no peptide coated, blocked with Biotin) | | | | | | | | | | | | |

SEQUENCE LISTING

```
<160> NUMBER OF SEQ ID NOS: 30

<210> SEQ ID NO 1
<211> LENGTH: 15
<212> TYPE: PRT
<213> ORGANISM: Artificial Sequence
<220> FEATURE:
<223> OTHER INFORMATION: NY-ESO-1 peptide

<400> SEQUENCE: 1

Gly Pro Gly Gly Pro Gly Ile Pro Asp Gly Pro Gly Gly Asn Ala
1               5                   10                  15

<210> SEQ ID NO 2
<211> LENGTH: 15
<212> TYPE: PRT
<213> ORGANISM: Artificial Sequence
<220> FEATURE:
<223> OTHER INFORMATION: NY-ESO-1 peptide

<400> SEQUENCE: 2

Gly Gly Ser Thr Gly Asp Ala Asp Gly Pro Gly Gly Pro Gly Ile
1               5                   10                  15

<210> SEQ ID NO 3
<211> LENGTH: 15
<212> TYPE: PRT
<213> ORGANISM: Artificial Sequence
<220> FEATURE:
<223> OTHER INFORMATION: NY-ESO-1 peptide

<400> SEQUENCE: 3

Ala Met Pro Phe Ala Thr Pro Met Glu Ala Glu Leu Ala Arg Arg
1               5                   10                  15

<210> SEQ ID NO 4
<211> LENGTH: 15
<212> TYPE: PRT
<213> ORGANISM: Artificial Sequence
```

-continued

```
<220> FEATURE:
<223> OTHER INFORMATION: NY-ESO-1 peptide

<400> SEQUENCE: 4

Gly Asp Ala Asp Gly Pro Gly Gly Pro Gly Ile Pro Asp Gly Pro
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: NY-ESO-1 peptide

<400> SEQUENCE: 5

Gly Gly Gly Ala Pro Arg Gly Pro His Gly Gly Ala Ala Ser Gly
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: NY-ESO-1 peptide

<400> SEQUENCE: 6

Ala Thr Pro Met Glu Ala Glu Leu Ala Arg Arg Ser Leu Ala Gln
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: NY-ESO-1 peptide

<400> SEQUENCE: 7

Pro Arg Gly Ala Gly Ala Ala Arg Ala Ser Gly Pro Gly Gly Gly
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: NY-ESO-1 peptide

<400> SEQUENCE: 8

Pro Gly Ile Pro Asp Gly Pro Gly Gly Asn Ala Gly Gly Pro Gly
1               5                   10                  15

<210> SEQ ID NO 9
<211> LENGTH: 15
<212> TYPE: PRT
<213> ORGANISM: Artificial Sequence
<220> FEATURE:
<223> OTHER INFORMATION: NY-ESO-1 peptide

<400> SEQUENCE: 9

Met Gln Ala Glu Gly Arg Gly Thr Gly Gly Ser Thr Gly Asp Ala
1               5                   10                  15

<210> SEQ ID NO 10
<211> LENGTH: 15
<212> TYPE: PRT
<213> ORGANISM: Artificial Sequence
<220> FEATURE:
```

```
<223> OTHER INFORMATION: NY-ESO-1 peptide

<400> SEQUENCE: 10

Pro Arg Gly Pro His Gly Gly Ala Ala Ser Gly Leu Asn Gly Cys
1               5                   10                  15

<210> SEQ ID NO 11
<211> LENGTH: 15
<212> TYPE: PRT
<213> ORGANISM: Artificial Sequence
<220> FEATURE:
<223> OTHER INFORMATION: p53 peptide

<400> SEQUENCE: 11

Leu Arg Lys Lys Gly Glu Pro His His Glu Leu Pro Pro Gly Ser
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: p53 peptide

<400> SEQUENCE: 12

Leu Ser Pro Asp Asp Ile Glu Gln Trp Phe Thr Glu Asp Pro Gly
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: p53 peptide

<400> SEQUENCE: 13

Met Glu Glu Pro Gln Ser Asp Pro Ser Val Glu Pro Pro Leu Ser
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: p53 peptide

<400> SEQUENCE: 14

Ser Val Thr Cys Thr Tyr Ser Pro Ala Leu Asn Lys Met Phe Cys
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Endoplasmin peptide

<400> SEQUENCE: 15

Cys Ala Leu Val Ala Ser Gln Tyr Gly Trp Ser Gly Asn Met Glu
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: K-Ras 2 peptide
```

```
<400> SEQUENCE: 16

Glu Asp Ser Tyr Arg Lys Gln Val Val Ile Asp Gly Glu Thr Cys
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: MAGE-1 peptide

<400> SEQUENCE: 17

Ser Ser Ser Ser Pro Leu Val Leu Gly Thr Leu Glu Glu Val Pro
1               5                   10                  15

<210> SEQ ID NO 18
<211> LENGTH: 15
<212> TYPE: PRT
<213> ORGANISM: Artificial Sequence
<220> FEATURE:
<223> OTHER INFORMATION: MAGE-3 peptide

<400> SEQUENCE: 18

Tyr Pro Leu Trp Ser Gln Ser Tyr Glu Asp Ser Ser Asn Gln Glu
1               5                   10                  15

<210> SEQ ID NO 19
<211> LENGTH: 15
<212> TYPE: PRT
<213> ORGANISM: Artificial Sequence
<220> FEATURE:
<223> OTHER INFORMATION: MAGE-4 peptide

<400> SEQUENCE: 19

Ser Ser Ser Ser Pro Leu Val Pro Gly Thr Leu Glu Glu Val Pro
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: TRIO and F-actin-binding protein peptide

<400> SEQUENCE: 20

Ala Gly Ala Phe Gln Ala Gln Asp Glu Gly Arg Ser Gln Gln Pro
1               5                   10                  15

<210> SEQ ID NO 21
<211> LENGTH: 15
<212> TYPE: PRT
<213> ORGANISM: Artificial Sequence
<220> FEATURE:
<223> OTHER INFORMATION: XAGE-1 peptide

<400> SEQUENCE: 21

Glu His Cys Lys Met Pro Glu Ala Gly Glu Glu Gln Pro Gln Val
1               5                   10                  15

<210> SEQ ID NO 22
<211> LENGTH: 180
<212> TYPE: PRT
<213> ORGANISM: Homo sapiens

<400> SEQUENCE: 22
```

Met Gln Ala Glu Gly Arg Gly Thr Gly Gly Ser Thr Gly Asp Ala Asp
1               5                   10                  15

Gly Pro Gly Gly Pro Gly Ile Pro Asp Gly Pro Gly Asn Ala Gly
            20                  25                  30

Gly Pro Gly Glu Ala Gly Ala Thr Gly Gly Arg Gly Pro Arg Gly Ala
            35                  40                  45

Gly Ala Ala Arg Ala Ser Gly Pro Gly Gly Ala Pro Arg Gly Pro
        50                  55                  60

His Gly Gly Ala Ala Ser Gly Leu Asn Gly Cys Cys Arg Cys Gly Ala
65                  70                  75                  80

Arg Gly Pro Glu Ser Arg Leu Leu Glu Phe Tyr Leu Ala Met Pro Phe
                85                  90                  95

Ala Thr Pro Met Glu Ala Glu Leu Ala Arg Arg Ser Leu Ala Gln Asp
            100                 105                 110

Ala Pro Pro Leu Pro Val Pro Gly Val Leu Leu Lys Glu Phe Thr Val
            115                 120                 125

Ser Gly Asn Ile Leu Thr Ile Arg Leu Thr Ala Ala Asp His Arg Gln
            130                 135                 140

Leu Gln Leu Ser Ile Ser Ser Cys Leu Gln Gln Leu Ser Leu Leu Met
145                 150                 155                 160

Trp Ile Thr Gln Cys Phe Leu Pro Val Phe Leu Ala Gln Pro Pro Ser
                165                 170                 175

Gly Gln Arg Arg
            180

<210> SEQ ID NO 23
<211> LENGTH: 393
<212> TYPE: PRT
<213> ORGANISM: Homo sapiens

<400> SEQUENCE: 23

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
        50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
            115                 120                 125

Ala Leu Asn Lys Met Phe Cys Gln Leu Ala Lys Thr Cys Pro Val Gln
            130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

-continued

His Leu Ile Arg Val Glu Gly Asn Leu Arg Val Glu Tyr Leu Asp Asp
         195                 200                 205

Arg Asn Thr Phe Arg His Ser Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390

<210> SEQ ID NO 24
<211> LENGTH: 189
<212> TYPE: PRT
<213> ORGANISM: Homo sapiens

<400> SEQUENCE: 24

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Arg Val Glu Asp Ala Phe Tyr Thr Leu Val
145                 150                 155                 160

Arg Glu Ile Arg Gln Tyr Arg Leu Lys Lys Ile Ser Lys Glu Glu Lys

```
                        165                 170                 175
Thr Pro Gly Cys Val Lys Ile Lys Cys Ile Ile Met
            180                 185

<210> SEQ ID NO 25
<211> LENGTH: 803
<212> TYPE: PRT
<213> ORGANISM: Homo sapiens

<400> SEQUENCE: 25

Met Arg Ala Leu Trp Val Leu Gly Leu Cys Cys Val Leu Leu Thr Phe
1               5                   10                  15

Gly Ser Val Arg Ala Asp Asp Glu Val Asp Val Asp Gly Thr Val Glu
            20                  25                  30

Glu Asp Leu Gly Lys Ser Arg Glu Gly Ser Arg Thr Asp Asp Glu Val
        35                  40                  45

Val Gln Arg Glu Glu Glu Ala Ile Gln Leu Asp Gly Leu Asn Ala Ser
    50                  55                  60

Gln Ile Arg Glu Leu Arg Glu Lys Ser Glu Lys Phe Ala Phe Gln Ala
65                  70                  75                  80

Glu Val Asn Arg Met Met Lys Leu Ile Ile Asn Ser Leu Tyr Lys Asn
                85                  90                  95

Lys Glu Ile Phe Leu Arg Glu Leu Ile Ser Asn Ala Ser Asp Ala Leu
            100                 105                 110

Asp Lys Ile Arg Leu Ile Ser Leu Thr Asp Glu Asn Ala Leu Ser Gly
        115                 120                 125

Asn Glu Glu Leu Thr Val Lys Ile Lys Cys Asp Lys Glu Lys Asn Leu
    130                 135                 140

Leu His Val Thr Asp Thr Gly Val Gly Met Thr Arg Glu Glu Leu Val
145                 150                 155                 160

Lys Asn Leu Gly Thr Ile Ala Lys Ser Gly Thr Ser Glu Phe Leu Asn
                165                 170                 175

Lys Met Thr Glu Ala Gln Glu Asp Gly Gln Ser Thr Ser Glu Leu Ile
            180                 185                 190

Gly Gln Phe Gly Val Gly Phe Tyr Ser Ala Phe Leu Val Ala Asp Lys
        195                 200                 205

Val Ile Val Thr Ser Lys His Asn Asn Asp Thr Gln His Ile Trp Glu
    210                 215                 220

Ser Asp Ser Asn Glu Phe Ser Val Ile Ala Asp Pro Arg Gly Asn Thr
225                 230                 235                 240

Leu Gly Arg Gly Thr Thr Ile Thr Leu Val Leu Lys Glu Glu Ala Ser
                245                 250                 255

Asp Tyr Leu Glu Leu Asp Thr Ile Lys Asn Leu Val Lys Lys Tyr Ser
            260                 265                 270

Gln Phe Ile Asn Phe Pro Ile Tyr Val Trp Ser Ser Lys Thr Glu Thr
        275                 280                 285

Val Glu Glu Pro Met Glu Glu Glu Ala Ala Lys Glu Glu Lys Glu
    290                 295                 300

Glu Ser Asp Asp Glu Ala Ala Val Glu Glu Glu Glu Lys Lys
305                 310                 315                 320

Pro Lys Thr Lys Lys Val Glu Lys Thr Val Trp Asp Trp Glu Leu Met
                325                 330                 335

Asn Asp Ile Lys Pro Ile Trp Gln Arg Pro Ser Lys Glu Val Glu Glu
            340                 345                 350
```

```
Asp Glu Tyr Lys Ala Phe Tyr Lys Ser Phe Ser Lys Glu Ser Asp Asp
            355                 360                 365
Pro Met Ala Tyr Ile His Phe Thr Ala Glu Gly Glu Val Thr Phe Lys
        370                 375                 380
Ser Ile Leu Phe Val Pro Thr Ser Ala Pro Arg Gly Leu Phe Asp Glu
385                 390                 395                 400
Tyr Gly Ser Lys Lys Ser Asp Tyr Ile Lys Leu Tyr Val Arg Arg Val
                405                 410                 415
Phe Ile Thr Asp Asp Phe His Asp Met Met Pro Lys Tyr Leu Asn Phe
            420                 425                 430
Val Lys Gly Val Val Asp Ser Asp Asp Leu Pro Leu Asn Val Ser Arg
        435                 440                 445
Glu Thr Leu Gln Gln His Lys Leu Leu Lys Val Ile Arg Lys Lys Leu
    450                 455                 460
Val Arg Lys Thr Leu Asp Met Ile Lys Lys Ile Ala Asp Asp Lys Tyr
465                 470                 475                 480
Asn Asp Thr Phe Trp Lys Glu Phe Gly Thr Asn Ile Lys Leu Gly Val
                485                 490                 495
Ile Glu Asp His Ser Asn Arg Thr Arg Leu Ala Lys Leu Leu Arg Phe
            500                 505                 510
Gln Ser Ser His His Pro Thr Asp Ile Thr Ser Leu Asp Gln Tyr Val
        515                 520                 525
Glu Arg Met Lys Glu Lys Gln Asp Lys Ile Tyr Phe Met Ala Gly Ser
    530                 535                 540
Ser Arg Lys Glu Ala Glu Ser Ser Pro Phe Val Glu Arg Leu Leu Lys
545                 550                 555                 560
Lys Gly Tyr Glu Val Ile Tyr Leu Thr Glu Pro Val Asp Glu Tyr Cys
                565                 570                 575
Ile Gln Ala Leu Pro Glu Phe Asp Gly Lys Arg Phe Gln Asn Val Ala
            580                 585                 590
Lys Glu Gly Val Lys Phe Asp Glu Ser Glu Lys Thr Lys Glu Ser Arg
        595                 600                 605
Glu Ala Val Glu Lys Glu Phe Glu Pro Leu Leu Asn Trp Met Lys Asp
    610                 615                 620
Lys Ala Leu Lys Asp Lys Ile Glu Lys Ala Val Val Ser Gln Arg Leu
625                 630                 635                 640
Thr Glu Ser Pro Cys Ala Leu Val Ala Ser Gln Tyr Gly Trp Ser Gly
                645                 650                 655
Asn Met Glu Arg Ile Met Lys Ala Gln Ala Tyr Gln Thr Gly Lys Asp
            660                 665                 670
Ile Ser Thr Asn Tyr Tyr Ala Ser Gln Lys Lys Thr Phe Glu Ile Asn
        675                 680                 685
Pro Arg His Pro Leu Ile Arg Asp Met Leu Arg Arg Ile Lys Glu Asp
    690                 695                 700
Glu Asp Asp Lys Thr Val Leu Asp Leu Ala Val Val Leu Phe Glu Thr
705                 710                 715                 720
Ala Thr Leu Arg Ser Gly Tyr Leu Leu Pro Asp Thr Lys Ala Tyr Gly
                725                 730                 735
Asp Arg Ile Glu Arg Met Leu Arg Leu Ser Leu Asn Ile Asp Pro Asp
            740                 745                 750
Ala Lys Val Glu Glu Glu Pro Glu Glu Pro Glu Glu Thr Ala Glu
        755                 760                 765
Asp Thr Thr Glu Asp Thr Glu Gln Asp Glu Asp Glu Glu Met Asp Val
```

```
            770                 775                 780
Gly Thr Asp Glu Glu Glu Thr Ala Lys Glu Ser Thr Ala Glu Lys
785                 790                 795                 800

Asp Glu Leu

<210> SEQ ID NO 26
<211> LENGTH: 2365
<212> TYPE: PRT
<213> ORGANISM: Homo sapiens

<400> SEQUENCE: 26

Met Glu Val Pro Gly Asp Ala Leu Cys Glu His Phe Glu Ala Asn
1               5                   10                  15

Ile Leu Thr Gln Asn Arg Cys Gln Asn Cys Phe His Pro Glu Glu Ala
                20                  25                  30

His Gly Ala Arg Tyr Gln Glu Leu Arg Ser Pro Ser Gly Ala Glu Val
                35                  40                  45

Pro Tyr Cys Asp Leu Pro Arg Cys Pro Ala Pro Glu Asp Pro Leu
    50                  55                  60

Ser Ala Ser Thr Ser Gly Cys Gln Ser Val Val Asp Pro Gly Leu Arg
65                  70                  75                  80

Pro Gly Pro Lys Arg Gly Pro Ser Pro Ser Ala Gly Leu Pro Glu Glu
                85                  90                  95

Gly Pro Thr Ala Ala Pro Arg Ser Arg Ser Arg Glu Leu Glu Ala Val
                100                 105                 110

Pro Tyr Leu Glu Gly Leu Thr Thr Ser Leu Cys Gly Ser Cys Asn Glu
    115                 120                 125

Asp Pro Gly Ser Asp Pro Thr Ser Ser Pro Asp Ser Ala Thr Pro Asp
130                 135                 140

Asp Thr Ser Asn Ser Ser Ser Val Asp Trp Asp Thr Val Glu Arg Gln
145                 150                 155                 160

Glu Glu Glu Ala Pro Ser Trp Asp Glu Leu Ala Val Met Ile Pro Arg
                165                 170                 175

Arg Pro Arg Glu Gly Pro Arg Ala Asp Ser Ser Gln Arg Ala Pro Ser
                180                 185                 190

Leu Leu Thr Arg Ser Pro Val Gly Gly Asp Ala Ala Gly Gln Lys Lys
    195                 200                 205

Glu Asp Thr Gly Gly Gly Arg Ser Ala Gly Gln His Trp Ala Arg
210                 215                 220

Leu Arg Gly Glu Ser Gly Leu Ser Leu Glu Arg His Arg Ser Thr Leu
225                 230                 235                 240

Thr Gln Ala Ser Ser Met Thr Pro His Ser Gly Pro Arg Ser Thr Thr
                245                 250                 255

Ser Gln Ala Ser Pro Ala Gln Arg Asp Thr Ala Gln Ala Ser Thr
                260                 265                 270

Arg Glu Ile Pro Arg Ala Ser Ser Pro His Arg Ile Thr Gln Arg Asp
    275                 280                 285

Thr Ser Arg Ala Ser Ser Thr Gln Gln Glu Ile Ser Arg Ala Ser Ser
    290                 295                 300

Thr Gln Gln Glu Thr Ser Arg Ala Ser Ser Gln Glu Asp Thr Pro
305                 310                 315                 320

Arg Ala Ser Ser Thr Gln Glu Asp Thr Pro Arg Ala Ser Ser Thr Gln
                325                 330                 335

Trp Asn Thr Pro Arg Ala Ser Ser Pro Ser Arg Ser Thr Gln Leu Asp
```

```
            340                 345                 350
Asn Pro Arg Thr Ser Ser Thr Gln Gln Asp Asn Pro Gln Thr Ser Phe
            355                 360                 365
Pro Thr Cys Thr Pro Gln Arg Glu Asn Pro Arg Thr Pro Cys Val Gln
            370                 375                 380
Gln Asp Asp Pro Arg Ala Ser Ser Pro Asn Arg Thr Thr Gln Arg Glu
385                 390                 395                 400
Asn Ser Arg Thr Ser Cys Ala Gln Arg Asp Asn Pro Lys Ala Ser Arg
            405                 410                 415
Thr Ser Ser Pro Asn Arg Ala Thr Arg Asp Asn Pro Arg Thr Ser Cys
            420                 425                 430
Ala Gln Arg Asp Asn Pro Arg Ala Ser Ser Pro Ser Arg Ala Thr Arg
            435                 440                 445
Asp Asn Pro Thr Thr Ser Cys Ala Gln Arg Asp Asn Pro Arg Ala Ser
            450                 455                 460
Arg Thr Ser Ser Pro Asn Arg Ala Thr Arg Asp Asn Pro Arg Thr Ser
465                 470                 475                 480
Cys Ala Gln Arg Asp Asn Pro Arg Ala Ser Ser Pro Ser Arg Ala Thr
            485                 490                 495
Arg Asp Asn Pro Thr Thr Ser Cys Ala Gln Arg Asp Asn Pro Arg Ala
            500                 505                 510
Ser Arg Thr Ser Ser Pro Asn Arg Ala Thr Arg Asp Asn Pro Arg Thr
            515                 520                 525
Ser Cys Ala Gln Arg Asp Asn Pro Arg Ala Ser Ser Pro Asn Arg Ala
            530                 535                 540
Ala Arg Asp Asn Pro Thr Thr Ser Cys Ala Gln Arg Asp Asn Pro Arg
545                 550                 555                 560
Ala Ser Arg Thr Ser Ser Pro Asn Arg Ala Thr Arg Asp Asn Pro Arg
            565                 570                 575
Thr Ser Cys Ala Gln Arg Asp Asn Pro Arg Ala Ser Ser Pro Asn Arg
            580                 585                 590
Ala Thr Arg Asp Asn Pro Thr Thr Ser Cys Ala Gln Arg Asp Asn Pro
            595                 600                 605
Arg Ala Ser Arg Thr Ser Ser Pro Asn Arg Ala Thr Arg Asp Asn Pro
            610                 615                 620
Arg Thr Ser Cys Ala Gln Arg Asp Asn Pro Arg Ala Ser Ser Pro Asn
625                 630                 635                 640
Arg Thr Thr Gln Gln Asp Ser Pro Arg Thr Ser Cys Ala Arg Arg Asp
            645                 650                 655
Asp Pro Arg Ala Ser Ser Pro Asn Arg Thr Ile Gln Gln Glu Asn Pro
            660                 665                 670
Arg Thr Ser Cys Ala Leu Arg Asp Asn Pro Arg Ala Ser Ser Pro Ser
            675                 680                 685
Arg Thr Ile Gln Gln Glu Asn Pro Arg Thr Ser Cys Ala Gln Arg Asp
            690                 695                 700
Asp Pro Arg Ala Ser Ser Pro Asn Arg Thr Thr Gln Gln Glu Asn Pro
705                 710                 715                 720
Arg Thr Ser Cys Ala Arg Arg Asp Asn Pro Arg Ala Ser Ser Arg Asn
            725                 730                 735
Arg Thr Ile Gln Arg Asp Asn Pro Arg Thr Ser Cys Ala Gln Arg Asp
            740                 745                 750
Asn Pro Arg Ala Ser Ser Pro Asn Arg Thr Ile Gln Gln Glu Asn Leu
            755                 760                 765
```

```
Arg Thr Ser Cys Thr Arg Gln Asp Asn Pro Arg Thr Ser Ser Pro Asn
    770                 775                 780

Arg Ala Thr Arg Asp Asn Pro Arg Thr Ser Cys Ala Gln Arg Asp Asn
785                 790                 795                 800

Leu Arg Ala Ser Ser Pro Ile Arg Ala Thr Gln Gln Asp Asn Pro Arg
                    805                 810                 815

Thr Cys Ile Gln Gln Asn Ile Pro Arg Ser Ser Ser Thr Gln Gln Asp
            820                 825                 830

Asn Pro Lys Thr Ser Cys Thr Lys Arg Asp Asn Leu Arg Pro Thr Cys
            835                 840                 845

Thr Gln Arg Asp Arg Thr Gln Ser Phe Ser Phe Gln Asp Asn Pro
    850                 855                 860

Gly Thr Ser Ser Ser Gln Cys Cys Thr Gln Lys Glu Asn Leu Arg Pro
865                 870                 875                 880

Ser Ser Pro His Arg Ser Thr Gln Trp Asn Asn Pro Arg Asn Ser Ser
                885                 890                 895

Pro His Arg Thr Asn Lys Asp Ile Pro Trp Ala Ser Phe Pro Leu Arg
            900                 905                 910

Pro Thr Gln Ser Asp Gly Pro Arg Thr Ser Ser Pro Ser Arg Ser Lys
            915                 920                 925

Gln Ser Glu Val Pro Trp Ala Ser Ile Ala Leu Arg Pro Thr Gln Gly
    930                 935                 940

Asp Arg Pro Gln Thr Ser Ser Pro Ser Arg Pro Ala Gln His Asp Pro
945                 950                 955                 960

Pro Gln Ser Ser Phe Gly Pro Thr Gln Tyr Asn Leu Pro Ser Arg Ala
                965                 970                 975

Thr Ser Ser Ser His Asn Pro Gly His Gln Ser Thr Ser Arg Thr Ser
                980                 985                 990

Ser Pro Val Tyr Pro Ala Ala Tyr Gly Ala Pro Leu Thr Ser Pro Glu
        995                 1000                1005

Pro Ser Gln Pro Pro Cys Ala Val Cys Ile Gly His Arg Asp Ala
        1010                1015                1020

Pro Arg Ala Ser Ser Pro Pro Arg Tyr Leu Gln His Asp Pro Phe
    1025                1030                1035

Pro Phe Phe Pro Glu Pro Arg Ala Pro Glu Ser Glu Pro Pro His
    1040                1045                1050

His Glu Pro Pro Tyr Ile Pro Pro Ala Val Cys Ile Gly His Arg
    1055                1060                1065

Asp Ala Pro Arg Ala Ser Ser Pro Pro Arg His Thr Gln Phe Asp
    1070                1075                1080

Pro Phe Pro Phe Leu Pro Asp Thr Ser Asp Ala Glu His Gln Cys
    1085                1090                1095

Gln Ser Pro Gln His Glu Pro Leu Gln Leu Pro Ala Pro Val Cys
    1100                1105                1110

Ile Gly Tyr Arg Asp Ala Pro Arg Ala Ser Ser Pro Pro Arg Gln
    1115                1120                1125

Ala Pro Glu Pro Ser Leu Leu Phe Gln Asp Leu Pro Arg Ala Ser
    1130                1135                1140

Thr Glu Ser Leu Val Pro Ser Met Asp Ser Leu His Glu Cys Pro
    1145                1150                1155

His Ile Pro Thr Pro Val Cys Ile Gly His Arg Asp Ala Pro Ser
    1160                1165                1170
```

-continued

```
Phe Ser Ser Pro Pro Arg Gln Ala Pro Glu Pro Ser Leu Phe Phe
1175                1180                1185

Gln Asp Pro Pro Gly Thr Ser Met Glu Ser Leu Ala Pro Ser Thr
1190                1195                1200

Asp Ser Leu His Gly Ser Pro Val Leu Ile Pro Gln Val Cys Ile
1205                1210                1215

Gly His Arg Asp Ala Pro Arg Ala Ser Ser Pro Arg His Pro
1220                1225                1230

Pro Ser Asp Leu Ala Phe Leu Ala Pro Ser Pro Ser Pro Gly Ser
1235                1240                1245

Ser Gly Gly Ser Arg Gly Ser Ala Pro Pro Gly Glu Thr Arg His
1250                1255                1260

Asn Leu Glu Arg Glu Glu Tyr Thr Val Leu Ala Asp Leu Pro Pro
1265                1270                1275

Pro Arg Arg Leu Ala Gln Arg Gln Pro Gly Pro Gln Ala Gln Cys
1280                1285                1290

Ser Ser Gly Gly Arg Thr His Ser Pro Gly Arg Ala Glu Val Glu
1295                1300                1305

Arg Leu Phe Gly Gln Glu Arg Arg Lys Ser Glu Ala Ala Gly Ala
1310                1315                1320

Phe Gln Ala Gln Asp Glu Gly Arg Ser Gln Gln Pro Ser Gln Gly
1325                1330                1335

Gln Ser Gln Leu Leu Arg Arg Gln Ser Ser Pro Ala Pro Ser Arg
1340                1345                1350

Gln Val Thr Met Leu Pro Ala Lys Gln Ala Glu Leu Thr Arg Arg
1355                1360                1365

Ser Gln Ala Glu Pro Pro His Pro Trp Ser Pro Glu Lys Arg Pro
1370                1375                1380

Glu Gly Asp Arg Gln Leu Gln Gly Ser Pro Leu Pro Pro Arg Thr
1385                1390                1395

Ser Ala Arg Thr Pro Glu Arg Glu Leu Arg Thr Gln Arg Pro Leu
1400                1405                1410

Glu Ser Gly Gln Ala Gly Pro Arg Gln Pro Leu Gly Val Trp Gln
1415                1420                1425

Ser Gln Glu Glu Pro Pro Gly Ser Gln Gly Pro His Arg His Leu
1430                1435                1440

Glu Arg Ser Trp Ser Ser Gln Glu Gly Gly Leu Gly Pro Gly Gly
1445                1450                1455

Trp Trp Gly Cys Gly Glu Pro Ser Leu Gly Ala Ala Lys Ala Pro
1460                1465                1470

Glu Gly Ala Trp Gly Gly Thr Ser Arg Glu Tyr Lys Glu Ser Trp
1475                1480                1485

Gly Gln Pro Glu Ala Trp Glu Glu Lys Pro Thr His Glu Leu Pro
1490                1495                1500

Arg Glu Leu Gly Lys Arg Ser Pro Leu Thr Ser Pro Pro Glu Asn
1505                1510                1515

Trp Gly Gly Pro Ala Glu Ser Ser Gln Ser Trp His Ser Gly Thr
1520                1525                1530

Pro Thr Ala Val Gly Trp Gly Ala Glu Gly Ala Cys Pro Tyr Pro
1535                1540                1545

Arg Gly Ser Glu Arg Arg Pro Glu Leu Asp Trp Arg Asp Leu Leu
1550                1555                1560

Gly Leu Leu Arg Ala Pro Gly Glu Gly Val Trp Ala Arg Val Pro
```

-continued

```
            1565                1570                1575
Ser Leu Asp Trp Glu Gly Leu Leu Glu Leu Leu Gln Ala Arg Leu
    1580                1585                1590

Pro Arg Lys Asp Pro Ala Gly His Arg Asp Asp Leu Ala Arg Ala
    1595                1600                1605

Leu Gly Pro Glu Leu Gly Pro Pro Gly Thr Asn Asp Val Pro Glu
    1610                1615                1620

Gln Glu Ser His Ser Gln Pro Glu Gly Trp Ala Glu Ala Thr Pro
    1625                1630                1635

Val Asn Gly His Ser Pro Ala Leu Gln Ser Gln Ser Pro Val Gln
    1640                1645                1650

Leu Pro Ser Pro Ala Cys Thr Ser Thr Gln Trp Pro Lys Ile Lys
    1655                1660                1665

Val Thr Arg Gly Pro Ala Thr Ala Thr Leu Ala Gly Leu Glu Gln
    1670                1675                1680

Thr Gly Pro Leu Gly Ser Arg Ser Thr Ala Lys Gly Pro Ser Leu
    1685                1690                1695

Pro Glu Leu Gln Phe Gln Pro Glu Glu Pro Glu Glu Ser Glu Pro
    1700                1705                1710

Ser Arg Gly Gln Asp Pro Leu Thr Asp Gln Lys Gln Ala Asp Ser
    1715                1720                1725

Ala Asp Lys Arg Pro Ala Glu Gly Lys Ala Gly Ser Pro Leu Lys
    1730                1735                1740

Gly Arg Leu Val Thr Ser Trp Arg Met Pro Gly Asp Arg Pro Thr
    1745                1750                1755

Leu Phe Asn Pro Phe Leu Leu Ser Leu Gly Val Leu Arg Trp Arg
    1760                1765                1770

Arg Pro Asp Leu Leu Asn Phe Lys Lys Gly Trp Met Ser Ile Leu
    1775                1780                1785

Asp Glu Pro Gly Glu Pro Pro Ser Pro Ser Leu Thr Thr Thr Ser
    1790                1795                1800

Thr Ser Gln Trp Lys Lys His Trp Phe Val Leu Thr Asp Ser Ser
    1805                1810                1815

Leu Lys Tyr Tyr Arg Asp Ser Thr Ala Glu Glu Ala Asp Glu Leu
    1820                1825                1830

Asp Gly Glu Ile Asp Leu Arg Ser Cys Thr Asp Val Thr Glu Tyr
    1835                1840                1845

Ala Val Gln Arg Asn Tyr Gly Phe Gln Ile His Thr Lys Asp Ala
    1850                1855                1860

Val Tyr Thr Leu Ser Ala Met Thr Ser Gly Ile Arg Arg Asn Trp
    1865                1870                1875

Ile Glu Ala Leu Arg Lys Thr Val Arg Pro Thr Ser Ala Pro Asp
    1880                1885                1890

Val Thr Lys Leu Ser Asp Ser Asn Lys Glu Asn Ala Leu His Ser
    1895                1900                1905

Tyr Ser Thr Gln Lys Gly Pro Leu Lys Ala Gly Glu Gln Arg Ala
    1910                1915                1920

Gly Ser Glu Val Ile Ser Arg Gly Gly Pro Arg Lys Ala Asp Gly
    1925                1930                1935

Gln Arg Gln Ala Leu Asp Tyr Val Glu Leu Ser Pro Leu Thr Gln
    1940                1945                1950

Ala Ser Pro Gln Arg Ala Arg Thr Pro Ala Arg Thr Pro Asp Arg
    1955                1960                1965
```

```
Leu Ala Lys Gln Glu Glu Leu Glu Arg Asp Leu Ala Gln Arg Ser
    1970            1975                1980

Glu Glu Arg Arg Lys Trp Phe Glu Ala Thr Asp Ser Arg Thr Pro
    1985            1990                1995

Glu Val Pro Ala Gly Glu Gly Pro Arg Arg Gly Leu Gly Ala Pro
    2000            2005                2010

Leu Thr Glu Asp Gln Gln Asn Arg Leu Ser Glu Glu Ile Glu Lys
    2015            2020                2025

Lys Trp Gln Glu Leu Glu Lys Leu Pro Leu Arg Glu Asn Lys Arg
    2030            2035                2040

Val Pro Leu Thr Ala Leu Leu Asn Gln Ser Arg Gly Glu Arg Arg
    2045            2050                2055

Gly Pro Pro Ser Asp Gly His Glu Ala Leu Glu Lys Glu Val Gln
    2060            2065                2070

Ala Leu Arg Ala Gln Leu Glu Ala Trp Arg Leu Gln Gly Glu Ala
    2075            2080                2085

Pro Gln Ser Ala Leu Arg Ser Gln Glu Asp Gly His Ile Pro Pro
    2090            2095                2100

Gly Tyr Ile Ser Gln Glu Ala Cys Glu Arg Ser Leu Ala Glu Met
    2105            2110                2115

Glu Ser Ser His Gln Gln Val Met Glu Glu Leu Gln Arg His His
    2120            2125                2130

Glu Arg Glu Leu Gln Arg Leu Gln Gln Glu Lys Glu Trp Leu Leu
    2135            2140                2145

Ala Glu Glu Thr Ala Ala Thr Ala Ser Ala Ile Glu Ala Met Lys
    2150            2155                2160

Lys Ala Tyr Gln Glu Glu Leu Ser Arg Glu Leu Ser Lys Thr Arg
    2165            2170                2175

Ser Leu Gln Gln Gly Pro Asp Gly Leu Arg Lys Gln His Gln Ser
    2180            2185                2190

Asp Val Glu Ala Leu Lys Arg Glu Leu Gln Val Leu Ser Glu Gln
    2195            2200                2205

Tyr Ser Gln Lys Cys Leu Glu Ile Gly Ala Leu Met Arg Gln Ala
    2210            2215                2220

Glu Glu Arg Glu His Thr Leu Arg Arg Cys Gln Gln Glu Gly Gln
    2225            2230                2235

Glu Leu Leu Arg His Asn Gln Glu Leu His Gly Arg Leu Ser Glu
    2240            2245                2250

Glu Ile Asp Gln Leu Arg Gly Phe Ile Ala Ser Gln Gly Met Gly
    2255            2260                2265

Asn Gly Cys Gly Arg Ser Asn Glu Arg Ser Ser Cys Glu Leu Glu
    2270            2275                2280

Val Leu Leu Arg Val Lys Glu Asn Glu Leu Gln Tyr Leu Lys Lys
    2285            2290                2295

Glu Val Gln Cys Leu Arg Asp Glu Leu Gln Met Met Gln Lys Asp
    2300            2305                2310

Lys Arg Phe Thr Ser Gly Lys Tyr Gln Asp Val Tyr Val Glu Leu
    2315            2320                2325

Ser His Ile Lys Thr Arg Ser Glu Arg Glu Ile Glu Gln Leu Lys
    2330            2335                2340

Glu His Leu Arg Leu Ala Met Ala Ala Leu Gln Glu Lys Glu Ser
    2345            2350                2355
```

Met Arg Asn Ser Leu Ala Glu
    2360            2365

<210> SEQ ID NO 27
<211> LENGTH: 309
<212> TYPE: PRT
<213> ORGANISM: Homo sapiens

<400> SEQUENCE: 27

Met Ser Leu Glu Gln Arg Ser Leu His Cys Lys Pro Glu Ala Leu
1               5                   10                  15

Glu Ala Gln Gln Glu Ala Leu Gly Leu Val Cys Val Gln Ala Ala Thr
                20                  25                  30

Ser Ser Ser Ser Pro Leu Val Leu Gly Thr Leu Glu Glu Val Pro Thr
            35                  40                  45

Ala Gly Ser Thr Asp Pro Pro Gln Ser Pro Gln Gly Ala Ser Ala Phe
        50                  55                  60

Pro Thr Thr Ile Asn Phe Thr Arg Gln Arg Gln Pro Ser Glu Gly Ser
65                  70                  75                  80

Ser Ser Arg Glu Glu Glu Gly Pro Ser Thr Ser Cys Ile Leu Glu Ser
                85                  90                  95

Leu Phe Arg Ala Val Ile Thr Lys Lys Val Ala Asp Leu Val Gly Phe
                100                 105                 110

Leu Leu Leu Lys Tyr Arg Ala Arg Glu Pro Val Thr Lys Ala Glu Met
            115                 120                 125

Leu Glu Ser Val Ile Lys Asn Tyr Lys His Cys Phe Pro Glu Ile Phe
        130                 135                 140

Gly Lys Ala Ser Glu Ser Leu Gln Leu Val Phe Gly Ile Asp Val Lys
145                 150                 155                 160

Glu Ala Asp Pro Thr Gly His Ser Tyr Val Leu Val Thr Cys Leu Gly
                165                 170                 175

Leu Ser Tyr Asp Gly Leu Leu Gly Asp Asn Gln Ile Met Pro Lys Thr
            180                 185                 190

Gly Phe Leu Ile Ile Val Leu Val Met Ile Ala Met Glu Gly Gly His
        195                 200                 205

Ala Pro Glu Glu Glu Ile Trp Glu Glu Leu Ser Val Met Glu Val Tyr
210                 215                 220

Asp Gly Arg Glu His Ser Ala Tyr Gly Glu Pro Arg Lys Leu Leu Thr
225                 230                 235                 240

Gln Asp Leu Val Gln Glu Lys Tyr Leu Glu Tyr Arg Gln Val Pro Asp
                245                 250                 255

Ser Asp Pro Ala Arg Tyr Glu Phe Leu Trp Gly Pro Arg Ala Leu Ala
            260                 265                 270

Glu Thr Ser Tyr Val Lys Val Leu Glu Tyr Val Ile Lys Val Ser Ala
        275                 280                 285

Arg Val Arg Phe Phe Phe Pro Ser Leu Arg Glu Ala Ala Leu Arg Glu
        290                 295                 300

Glu Glu Glu Gly Val
305

<210> SEQ ID NO 28
<211> LENGTH: 314
<212> TYPE: PRT
<213> ORGANISM: Homo sapiens

<400> SEQUENCE: 28

-continued

```
Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
            115                 120                 125

Pro Val Thr Lys Ala Glu Met Leu Gly Ser Val Val Gly Asn Trp Gln
        130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
            195                 200                 205

Ile Ala Arg Glu Gly Asp Cys Ala Pro Glu Glu Lys Ile Trp Glu Glu
        210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
        290                 295                 300

His Glu Trp Val Leu Arg Glu Gly Glu Glu
305                 310

<210> SEQ ID NO 29
<211> LENGTH: 317
<212> TYPE: PRT
<213> ORGANISM: Homo sapiens

<400> SEQUENCE: 29

Met Ser Ser Glu Gln Lys Ser Gln His Cys Lys Pro Glu Glu Gly Val
1               5                   10                  15

Glu Ala Gln Glu Glu Ala Leu Gly Leu Val Gly Ala Gln Ala Pro Thr
            20                  25                  30

Thr Glu Glu Gln Glu Ala Ala Val Ser Ser Ser Pro Leu Val Pro
        35                  40                  45

Gly Thr Leu Glu Glu Val Pro Ala Ala Glu Ser Ala Gly Pro Pro Gln
50                  55                  60
```

```
Ser Pro Gln Gly Ala Ser Ala Leu Pro Thr Thr Ile Ser Phe Thr Cys
 65                  70                  75                  80

Trp Arg Gln Pro Asn Glu Gly Ser Ser Gln Glu Glu Glu Gly Pro
                 85                  90                  95

Ser Thr Ser Pro Asp Ala Glu Ser Leu Phe Arg Glu Ala Leu Ser Asn
                100                 105                 110

Lys Val Asp Glu Leu Ala His Phe Leu Leu Arg Lys Tyr Arg Ala Lys
                115                 120                 125

Glu Leu Val Thr Lys Ala Glu Met Leu Glu Arg Val Ile Lys Asn Tyr
                130                 135                 140

Lys Arg Cys Phe Pro Val Ile Phe Gly Lys Ala Ser Glu Ser Leu Lys
145                 150                 155                 160

Met Ile Phe Gly Ile Asp Val Lys Glu Val Asp Pro Ala Ser Asn Thr
                165                 170                 175

Tyr Thr Leu Val Thr Cys Leu Gly Leu Ser Tyr Asp Gly Leu Leu Gly
                180                 185                 190

Asn Asn Gln Ile Phe Pro Lys Thr Gly Leu Leu Ile Ile Val Leu Gly
                195                 200                 205

Thr Ile Ala Met Glu Gly Asp Ser Ala Ser Glu Glu Glu Ile Trp Glu
210                 215                 220

Glu Leu Gly Val Met Gly Val Tyr Asp Gly Arg Glu His Thr Val Tyr
225                 230                 235                 240

Gly Glu Pro Arg Lys Leu Leu Thr Gln Asp Trp Val Gln Glu Asn Tyr
                245                 250                 255

Leu Glu Tyr Arg Gln Val Pro Gly Ser Asn Pro Ala Arg Tyr Glu Phe
                260                 265                 270

Leu Trp Gly Pro Arg Ala Leu Ala Glu Thr Ser Tyr Val Lys Val Leu
                275                 280                 285

Glu His Val Val Arg Val Asn Ala Arg Val Arg Ile Ala Tyr Pro Ser
                290                 295                 300

Leu Arg Glu Ala Ala Leu Leu Glu Glu Glu Gly Val
305                 310                 315

<210> SEQ ID NO 30
<211> LENGTH: 81
<212> TYPE: PRT
<213> ORGANISM: Homo sapiens

<400> SEQUENCE: 30

Met Glu Ser Pro Lys Lys Lys Asn Gln Gln Leu Lys Val Gly Ile Leu
 1               5                  10                  15

His Leu Gly Ser Arg Gln Lys Lys Ile Arg Ile Gln Leu Arg Ser Gln
                20                  25                  30

Cys Ala Thr Trp Lys Val Ile Cys Lys Ser Cys Ile Ser Gln Thr Pro
                35                  40                  45

Gly Ile Asn Leu Asp Leu Gly Ser Gly Val Lys Val Lys Ile Ile Pro
                50                  55                  60

Lys Glu Glu His Cys Lys Met Pro Glu Ala Gly Glu Glu Gln Pro Gln
 65                  70                  75                  80

Val
```

METHODS AND KITS FOR THE DIAGNOSIS OF CANCER

CROSS-REFERENCE TO RELATED PATENT APPLICATIONS

This application is a national phase application of International Application No. PCT/EP2015/058179, which was filed Apr. 15, 2015, and which claims the benefit of the filing date of International Application No. PCT/EP2014/060096, which was filed on May 16, 2014. The content of these earlier filed applications is hereby incorporated by reference in its entirety.

SEQUENCE LISTING

The present application contains a Sequence Listing that has been submitted in ASCII format via EFS-Web on Jul. 11, 2017, containing the file name "37592_0004U1_Revised_Sequence_Listing.txt," which is 49,152 bytes in size, created on Jul. 10, 2017, and is hereby incorporated by reference pursuant to 37 C.F.R. § 1.52(e)(5).

TECHNICAL FIELD OF THE INVENTION

The present invention relates to methods and kits for the diagnosis, prognosis and/or monitoring of cancer in a patient. The present invention further relates to isolated peptides, panels of isolated peptides and diagnostic devices.

BACKGROUND OF THE INVENTION

Cancers figure among the leading causes of death worldwide, accounting for 8.2 million deaths in 2012 (Globocan 2012, IARC). It is expected that annual cancer cases will rise from 14 million in 2012 to 22 million in the next two decades (Globocan 2012, IARC).

As an example, lung cancer causes about 25% of all cancer-related mortality, wherein 80-90% of lung cancers are estimated to be caused by smoking. In light of the poor prognosis and limited treatment options for lung cancer patients at the time of diagnosis, early detection of lung cancer and surgical treatment are key to improving the outlook for lung cancer patients.

At the time of diagnosis, the majority of lung cancer cases present themselves as advanced cancer, often having metastasized to distant regions. Between 50%-60% of small cell lung cancer (SCLC) and non-small cell lung cancer (NSCLC) cases are detected at stage IV, while only a small fraction (~6%) of tumors are detected at early stages, often by chance and because of unrelated symptoms. Lung cancer detected at stage I has a >70% five year survival rate, while the outlook for patients to survive five years following primary diagnosis at stage IV is only at around 2%. These numbers clearly indicate the need for lung cancer early detection programs, as shifting the time of diagnosis to stage I tumors would have an immediate impact on the overall survival rates.

For many years researchers have published studies on serum markers that may have the potential to be used for the diagnosis of lung cancer at early stages. Among these markers autoantibodies that are generated by lung cancer patients against their tumor-associated antigens have been the most promising ones (see references [1], [2], [3], and [4] for examples and a general overview). Nevertheless, until now, no serum or plasma based in vitro diagnostic device (IVDD) has been established or has been widely accepted for the early diagnosis of lung cancer in a screening population. This may be due to the heterogeneity of the disease which impedes an effective diagnosis by a single test.

Another major reason is the low acceptance of diagnostic devices that cause too many false-positives in a screening population. False-positive results cause unnecessary anxiety in the diagnosed individuals and lead to low acceptance by physicians and health care providers because laborious and costly second and third diagnoses are required. The key indicators for physicians and health care providers are the positive and negative predictive value (PPV and NPV, respectively) that define the reliability of a positive or negative test result (dependent on the prevalence of the respective disease in the chosen screening population). A PPV of 20% means that among ten positive test results only two are correct (true-positives), whereas eight are wrong (false-positives) which is usually not acceptable in a screening program for above stated reasons. NPVs are usually high anyway due to the low abundance of a disease in a screening population (e.g. lung cancer at early stages with a prevalence of 1:300 in smoker or approximately 1:36 in smoker >65 years). PPVs below 30-35% are usually unacceptable and not cost-effective. For example, the widely accepted Pap-test for detection of cervical neoplasia has PPVs of >30% (refer to [5] and [6]).

Another example is the U.S. National Lung Screening Trial (NLST; [7]). This study was an 8 year lung cancer screening program comparing low dose computer tomography (LDCT) to chest X-ray in 50,000 smokers (age 50-74). The trial showed 20% reduced mortality in the LDCT cohort but not in the X-ray cohort. However, using LDCT caused 25% of study participants to receive follow-up procedures, which turned out not to be related to lung cancer. Due to this high false-positive rate or low specificity of LDCT, the PPV was ≤4%, meaning that 96 of 100 positive LDCT-results were false-positive. This implies high costs to the health care system when LDCT would be used as a routine screening tool (approximately $240,000 per saved life; [8]) which prevents insurance companies from reimbursing this procedure.

Taken together, PPVs greater than 30% are a prerequisite for the acceptance of a diagnostic device as a screening tool. Some examples of published data of lung cancer screening approaches are shown in Table 1 where specificity and sensitivity of the respective study are listed. PPV and NPV can be calculated for all of these data assuming a target screening population that is at high risk for developing lung cancer. PPVs are significantly below 30% in all cases although a high risk subpopulation (smokers >65 years with a prevalence of lung cancer of 2.8%) was chosen. A second weakness of the data are the relatively low numbers of analyzed samples that do not represent the real screening situation in clinical practice.

TABLE 1

Examples of published data of lung cancer screening approaches and corresponding hypothetical PPVs and NPVs.

| Source | Specificity | Sensitivity | Positive predictive value PPV* | Negative predictive value NPV* | Number of analyzed blood samples | |
|---|---|---|---|---|---|---|
| | | | | | Healthy donors | Lung carcinoma |
| [9] | 95% | 55% | 24% | 99% | 62 | 63 |
| [10] | 82% | 51% | 8% | 98% | 85 | 85 |
| [11] | 90% | 47% | 12% | 98% | 50 | 40 |

TABLE 1-continued

Examples of published data of lung cancer screening approaches and corresponding hypothetical PPVs and NPVs.

| Source | Specificity | Sensitivity | Positive predictive value PPV* | Negative predictive value NPV* | Number of analyzed blood samples | |
|---|---|---|---|---|---|---|
| | | | | | Healthy donors | Lung carcinoma |
| [12] | 92% | 76% | 22% | 99% | 50 | 104 |
| [13] | 89% | 39% | 9% | 98% | 235 | 235 |
| | 91% | 41% | 12% | 98% | | |
| [14] | 89% | 36% | 9% | 98% | n.a. | n.a. |

*Calculated for a high risk population of lung cancer (smokers > 65 years, prevalence 2.8% according to Robert-Koch-Institute "Cancer in Germany" 2008, published 2012)

The low PPVs calculated from published data are mainly due to the fact that usually specificities ≤95% are achieved (Table 1). The high impact of specificity on the PPV is demonstrated hypothetically in FIG. 1 and Table 2. At a given sensitivity (for example 25%) the PPV can be more than doubled by increasing specificity only by 2 percent points from 97% to 99% (PPV increases from 19.4% to 41.9%). In contrast, sensitivity must be doubled (from 25% to 50%) to have a similar effect on the PPV (increases from 12.6% to 22.4%).

TABLE 2

Hypothetical values to demonstrate influence of specificity on PPVs and NPVs.

| Prevalence* | Specificity | Sensitivity | Positive predictive value PPV | Negative predictive values NPV |
|---|---|---|---|---|
| 2.8% | 99.0% | 25.0% | 41.9% | 97.9% |
| | 98.0% | 25.0% | 26.5% | 97.8% |
| | 97.0% | 25.0% | 19.4% | 97.8% |
| | 96.0% | 25.0% | 15.3% | 97.8% |
| | 95.0% | 25.0% | 12.6% | 97.8% |
| | 95.0% | 50.0% | 22.4% | 98.5% |

*Calculated for a high risk population of lung cancer (smokers >65 years, prevalence 2.8% according to Robert-Koch-Institute "Cancer in Germany" 2008, published 2012)

If specificity drops below 98%, sensitivity must be greater than 50% to achieve PPVs >30%. This is true even if the risk population (smokers at all ages with a prevalence of 1:300) is further enriched (smokers at age >65 years with a prevalence of 1:36=2.8%). Sensitivities >50% at reasonable specificities are hardly ever achieved in screening programs for heterogeneous diseases like lung cancer.

In conclusion, a specificity of approximately 98-99% is necessary to achieve PPVs >30% for lung cancer screening even for high risk subpopulations. High PPVs in turn are a prerequisite for establishing a diagnostic device used for screening programs as described above. The lower the prevalence of the disease, the higher the specificity must be. Otherwise, the PPV is too low, and too many false-positives cause high costs and low acceptance.

Accordingly, it was an object of the present invention to provide methods and kits for the diagnosis, prognosis and/or monitoring of cancer, in particular lung cancer, in a patient, which facilitate a specificity of at least 97.5%, preferably 98-99%, and a positive predictive value (PPV) of >30%.

SUMMARY OF THE INVENTION

In one aspect, the invention relates to a method for the diagnosis, prognosis and/or monitoring of cancer in a patient, the method comprising the detection and/or determination of the amount of autoantibodies specifically binding to a panel of tumor-associated antigens in a biological sample isolated from the patient, wherein the panel of tumor-associated antigens comprises one or more tumor-associated antigens selected from the group consisting of NY-ESO-1, p53, K-Ras 2, Endoplasmin, TRIO and F-actin-binding protein, MAGE-1, MAGE-3, MAGE-4 and XAGE-1 and wherein the method facilitates a specificity of at least 97.5%, preferably at least 98%, and a sensitivity of at least 23%, preferably at least 24%.

In one embodiment, the panel of tumor-associated antigens comprises at least 2, preferably at least 3, more preferably at least 4, more preferably at least 5, more preferably at least 6, more preferably at least 7, even more preferably all of the tumor-associated antigens NY-ESO-1, p53, K-Ras 2, Endoplasmin, TRIO and F-actin-binding protein, MAGE-1, MAGE-3, MAGE-4 and XAGE-1.

In one embodiment, the detection and/or determination of the amount of autoantibodies takes place by screening the biological sample for autoantibodies specifically binding to a panel of isolated peptides, wherein the panel of isolated peptides comprises one or more isolated peptides consisting of 8 to 25, preferably 10 to 20, more preferably 12 to 18 amino acid residues and comprising at least 8, preferably at least 10, more preferably at least 12 contiguous amino acid residues of an amino acid sequence selected from the group consisting of SEQ ID NOs: 1 to 21.

In a further aspect, the invention relates to a method for the diagnosis, prognosis and/or monitoring of cancer in a patient, the method comprising the detection and/or determination of the amount of autoantibodies specifically binding to a panel of isolated peptides, wherein the panel of isolated peptides comprises one or more isolated peptides consisting of 8 to 25, preferably 10 to 20, more preferably 12 to 18 amino acid residues and comprising at least 8, preferably at least 10, more preferably at least 12 contiguous amino acid residues of an amino acid sequence selected from the group consisting of SEQ ID NOs: 1 to 21.

In one embodiment of the above methods, the panel of isolated peptides comprises one or more isolated peptides selected from the group consisting of SEQ ID NOs: 1 to 21.

In one embodiment of the above methods, the panel of isolated peptides comprises a plurality of isolated peptides as defined above.

In one embodiment, the panel of isolated peptides comprises at least one isolated peptide for each of at least 3, at least 5, at least 10, at least 15, at least 16, at least 17, at least 18, at least 19 or at least 20 of SEQ ID NOs: 1 to 21, preferably, for each of SEQ ID NOs: 1 to 21.

In one embodiment, the panel of isolated peptides comprises at least 3, at least 5, at least 10, at least 15, at least 16, at least 17, at least 18, at least 19 or at least 20 isolated peptides selected from the group consisting of SEQ ID NOs: 1 to 21. In one embodiment, the panel of isolated peptides comprises each of SEQ ID NOs: 1 to 21.

In one embodiment, the presence of the autoantibodies and/or an amount of the autoantibodies which is above a pre-defined cut-off value indicates the presence of cancer or an increased risk of developing cancer.

In one embodiment, the detection and/or determination of the amount of autoantibodies takes place with an immunoassay.

In one embodiment, the detection and/or determination of the amount of the autoantibodies comprises:

(i) contacting the biological sample with a panel of isolated peptides comprising one or more, preferably a plurality of, isolated peptides as defined above, and
(ii) detecting the formation of complexes between the one or more, preferably a plurality of, isolated peptides and the autoantibodies.

In one embodiment, the one or more, preferably the plurality of, isolated peptides are immobilized on a support.

In one embodiment, the biological sample comprises body fluid and/or body tissue.

In one embodiment, the body fluid is blood serum or blood plasma.

In one embodiment, the cancer is selected from the group consisting of lung cancer, colon cancer, gastric cancer, breast cancer, prostate cancer and melanoma.

In one embodiment, the cancer is lung cancer, preferably early stage lung cancer.

In a further aspect, the invention relates to an isolated peptide consisting of 8 to 25, preferably 10 to 20, more preferably 12 to 18 amino acid residues and comprising at least 8, preferably at least 10, more preferably at least 12 contiguous amino acid residues of an amino acid sequence selected from the group consisting of SEQ ID NOs: 1 to 21.

In one embodiment, the isolated peptide has an amino acid sequence selected from the group consisting of SEQ ID NOs: 1 to 21.

In a further aspect, the invention relates to a nucleic acid molecule encoding an isolated peptide as defined above, to an expression vector comprising said nucleic acid molecule or to a host cell comprising said nucleic acid molecule or said expression vector.

In a further aspect, the invention relates to a panel of isolated peptides comprising a plurality of isolated peptides as defined above, wherein, preferably, the panel comprises at least one isolated peptide for each of at least 3, at least 5, at least 10, at least 15, at least 16, at least 17, at least 18, at least 19 or at least 20 of SEQ ID NOs: 1 to 21, preferably, for each of SEQ ID NOs: 1 to 21.

In a further aspect, the invention relates to a diagnostic device comprising an isolated peptide as defined above or a panel of isolated peptides as defined above, wherein, preferably, the isolated peptide or panel of isolated peptides is immobilized on a support.

In one embodiment, the diagnostic device is a multi-well plate.

In a further aspect, the invention relates to a kit comprising an isolated peptide as defined above or a panel of isolated peptides as defined above or a diagnostic device as defined above.

In one embodiment, the kit further comprises instructions for use of the kit in a method for the diagnosis, prognosis and/or monitoring of cancer in a patient.

In one embodiment, the method is a method as defined above.

In one embodiment, the kit further comprises a reagent for detecting complex formation between an autoantibody and the isolated peptide or panel of isolated peptides.

In one embodiment, the reagent comprises a detectably labeled binding partner for the autoantibody.

In one embodiment, the binding partner for the autoantibody is an anti-immunoglobulin antibody, in particular an anti-human immunoglobulin antibody coupled to a detectable marker such as an enzyme. In one embodiment, the kit may further comprise an enzyme substrate.

In a further aspect, the invention relates to the isolated peptide as defined above, the panel of isolated peptides as defined above, the diagnostic device as defined above, or the kit as defined above for use in a method for the diagnosis, prognosis and/or monitoring of cancer in a patient.

In one embodiment, the method is a method as defined above.

In one embodiment, the cancer is selected from the group consisting of lung cancer, colon cancer, gastric cancer, breast cancer, prostate cancer and melanoma.

In one embodiment, the cancer is lung cancer, preferably early stage lung cancer.

In a further aspect, the invention relates to a method of treating cancer in a patient comprising the steps of:
(i) diagnosing and/or monitoring cancer in the patient according to the method as defined above;
(ii) treating the cancer in the patient.

In one embodiment, the treatment of the cancer comprises one or more selected from the group consisting of surgery, chemotherapy, hormonal therapy, radiation therapy and immunotherapy/targeted therapy.

In one embodiment, the cancer is selected from the group consisting of lung cancer, colon cancer, gastric cancer, breast cancer, prostate cancer and melanoma.

In one embodiment, the cancer is lung cancer, preferably early stage lung cancer.

BRIEF DESCRIPTION OF THE FIGURES

FIG. 7 shows the layout of a peptide-coated 96-well (ELISA-)immunoplate according to the present invention.

DETAILED DESCRIPTION OF THE INVENTION

Figure 1:
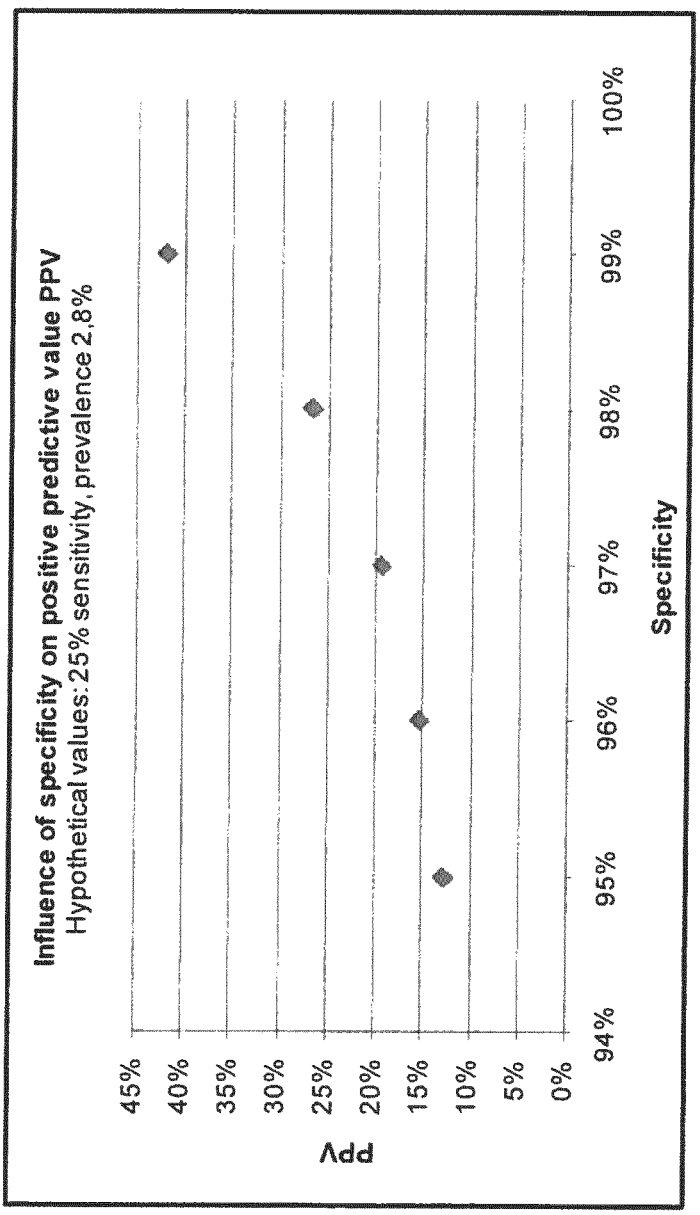
FIG. 1 shows the correlation between specificity and the positive predictive value (PPV).

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Preferably, the terms used herein are defined as described in "A multilingual glossary of biotechnological terms: (IUPAC Recommendations)", H. G. W. Leuenberger, B. Nagel, and H. Kölbl, Eds., Helvetica Chimica Acta, CH-4010 Basel, Switzerland, (1995).

The practice of the present invention will employ, unless otherwise indicated, conventional methods of chemistry, biochemistry, cell biology, immunology, and recombinant DNA techniques which are explained in the literature in the field (cf., e.g., *Molecular Cloning: A Laboratory Manual*, $2^{nd}$ Edition, J. Sambrook et al. eds., Cold Spring Harbor Laboratory Press, Cold Spring Harbor 1989).

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents are cited throughout the text of this specification. Each of the documents cited herein (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention.

As used herein, "cancer" includes a disease characterized by aberrantly regulated cellular growth, proliferation, differentiation, adhesion, and/or migration. The term "cancer" according to the invention comprises leukemias, seminomas, melanomas, teratomas, lymphomas, neuroblastomas, gliomas, rectal cancer, endometrial cancer, kidney cancer, adrenal cancer, thyroid cancer, blood cancer, skin cancer, cancer of the brain, cervical cancer, intestinal cancer, liver cancer, colon cancer, gastric cancer, intestine cancer, head and neck cancer, gastrointestinal cancer, lymph node cancer, esophagus cancer, colorectal cancer, pancreas cancer, ear, nose and throat (ENT) cancer, breast cancer, prostate cancer, cancer of the uterus, ovarian cancer and lung cancer and the metastases thereof. The term cancer according to the invention also comprises cancer metastases. According to the present invention, the cancer is preferably selected from the group consisting of lung cancer, colon cancer, gastric cancer, breast cancer, prostate cancer and melanoma. In one particular embodiment, the cancer is lung cancer, preferably early stage lung cancer.

Lung cancers are mostly carcinomas, i.e. malignancies that arise from epithelial cells, and are classified according to their histological type. For therapeutic purposes, two broad classes are distinguished: non-small cell lung carcinoma (NSCLC) and small cell lung carcinoma (SCLC). The three main subtypes of NSCLC are adenocarcinoma, squamous-cell carcinoma and large-cell carcinoma.

Lung cancer staging is the assessment of the extent to which a lung cancer has spread from its original source. As with most cancers, staging/grading is an important determinant of treatment and prognosis, wherein, in general, more advanced stages of cancer are less amenable to treatment and have a worse prognosis. The so called TNM classification is based on the size of the primary tumor, lymph node involvement and distant metastasis, and comprises the following stages: 0, IA, IB, IIA, IIB, IIIA, IIIB and IV. The term "early stage lung cancer", as used herein, refers to lung cancer of stages IA to IIB (i.e. stages I and II), preferably stages IB to IIB.

The term "patient", as used herein, includes humans, non-human primates or another animals, especially mammals such as cow, horse, pig, sheep, goat, dog, cat or rodent such as mouse and rat. In a particularly preferred embodiment, the patient is a human.

The term "antibody" refers to a glycoprotein comprising at least two heavy (H) chains and two light (L) chains inter-connected by disulfide bonds. Each heavy chain is comprised of a heavy chain variable region (abbreviated herein as VH) and a heavy chain constant region. Each light chain is comprised of a light chain variable region (abbreviated herein as VL) and a light chain constant region. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "autoantibody" generally relates to an antibody manufactured by an individual's immune system that is directed against one or more of the individual's own proteins, more particularly against one or more endogenous antigens. In particular, the term "autoantibody" relates according to the invention to an antibody which is directed against a tumor-associated antigen described herein and in particular specifically binds thereto.

The term "tumor-associated antigen", as used herein, refers to an antigenic protein or peptide produced in (and presented by) tumor cells and triggering an immune response in the host. According to the present invention, particularly preferred tumor-associated antigens include NY-ESO-1 (Accession No. P78358), p53 (Accession No. P04637), K-Ras 2 (Accession No. P01116), Endoplasmin (Accession No. P14625), TRIO and F-actin-binding protein (Accession No. Q9H2D6), Melanoma-associated antigen 1 (MAGE-1; Accession No. P43355), Melanoma-associated antigen 3 (MAGE-3; Accession No. P43357), Melanoma-associated antigen 4 (MAGE-4; Accession No. P43358) and X antigen family member 1 (XAGE-1; Accession No. Q9HD64).

In one embodiment, term "NY-ESO-1" relates to a protein comprising, preferably consisting of the amino acid sequence of SEQ ID NO: 22 of the sequence listing or a variant of said amino acid sequence. In one embodiment, term "p53" relates to a protein comprising, preferably consisting of the amino acid sequence of SEQ ID NO: 23 of the sequence listing or a variant of said amino acid sequence. In one embodiment, term "K-Ras 2" relates to a protein comprising, preferably consisting of the amino acid sequence of SEQ ID NO: 24 of the sequence listing or a variant of said amino acid sequence. In one embodiment, term "Endoplasmin" relates to a protein comprising, preferably consisting of the amino acid sequence of SEQ ID NO: 25 of the sequence listing or a variant of said amino acid sequence. In one embodiment, term "TRIO and F-actin-binding protein" relates to a protein comprising, preferably consisting of the amino acid sequence of SEQ ID NO: 26 of the sequence listing or a variant of said amino acid sequence. In one embodiment, term "Melanoma-associated antigen 1" relates to a protein comprising, preferably consisting of the amino acid sequence of SEQ ID NO: 27 of the sequence listing or a variant of said amino acid sequence. In one embodiment, term "Melanoma-associated antigen 3" relates to a protein comprising, preferably consisting of the amino acid sequence of SEQ ID NO: 28 of the sequence listing or a variant of said amino acid sequence. In one embodiment, term "Melanoma-associated antigen 4" relates to a protein comprising, preferably consisting of the amino acid sequence of SEQ ID NO: 29 of the sequence listing or a variant of said amino acid sequence. In one embodiment, the term "X antigen family member 1" relates to a protein comprising, preferably consisting of the amino acid sequence of SEQ ID NO: 30.

The term "variant" according to the invention refers, in particular, to mutants, splice variants, conformations, isoforms, allelic variants, species variants and species homologs, in particular those which are naturally present. An allelic variant relates to an alteration in the normal sequence of a gene, the significance of which is often unclear. Complete gene sequencing often identifies numerous allelic variants for a given gene. A species homolog is a nucleic acid or amino acid sequence with a different species of origin from that of a given nucleic acid or amino acid sequence. The term "variant" shall encompass any posttranslationally modified variants and conformation variants.

For the purposes of the present invention, "variants" of an amino acid sequence comprise amino acid insertion variants, amino acid addition variants, amino acid deletion variants and/or amino acid substitution variants.

Preferably the degree of similarity, preferably identity between a given amino acid sequence and an amino acid sequence which is a variant of said given amino acid sequence will be at least about 60%, 65%, 70%, 80%, 81%, 82%, 83%, 84%, 85%, 86%, 87%, 88%, 89%, 90%, 91%, 92%, 93%, 94%, 95%, 96%, 97%, 98%, or 99%. The degree of similarity or identity is given preferably for an amino acid region which is at least about 10%, at least about 20%, at least about 30%, at least about 40%, at least about 50%, at least about 60%, at least about 70%, at least about 80%, at least about 90% or about 100% of the entire length of the reference amino acid sequence. For example, if the reference amino acid sequence consists of 200 amino acids, the degree of similarity or identity is given preferably for at least about 20, at least about 40, at least about 60, at least about 80, at least about 100, at least about 120, at least about 140, at least about 160, at least about 180, or about 200 amino acids, preferably continuous amino acids. In preferred embodiments, the degree of similarity or identity is given for the entire length of the reference amino acid sequence. The alignment for determining sequence similarity, preferably sequence identity can be done with art known tools, preferably using the best sequence alignment, for example, using Align, using standard settings, preferably EMBOSS::needle, Matrix: Blosum62, Gap Open 10.0, Gap Extend 0.5.

"Sequence similarity" indicates the percentage of amino acids that either are identical or that represent conservative amino acid substitutions. "Sequence identity" between two amino acid sequences indicates the percentage of amino acids that are identical between the sequences.

The term "percentage identity" is intended to denote a percentage of amino acid residues which are identical between the two sequences to be compared, obtained after the best alignment, this percentage being purely statistical and the differences between the two sequences being distributed randomly and over their entire length. Sequence comparisons between two amino acid sequences are conventionally carried out by comparing these sequences after having aligned them optimally, said comparison being carried out by segment or by "window of comparison" in order to identify and compare local regions of sequence similarity. The optimal alignment of the sequences for comparison may be produced, besides manually, by means of the local homology algorithm of Smith and Waterman, 1981, Ads App. Math. 2, 482, by means of the local homology algorithm of Neddleman and Wunsch, 1970, J. Mol. Biol. 48, 443, by means of the similarity search method of Pearson and Lipman, 1988, Proc. Natl Acad. Sci. USA 85, 2444, or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.). The percentage identity is calculated by determining the number of identical positions between the two sequences being compared, dividing this number by the number of positions compared and multiplying the result obtained by 100 so as to obtain the percentage identity between these two sequences.

The term "detection and/or determination of the amount" in relation to a substance relates according to the invention to the determination of the occurrence or absence and/or the absolute and/or relative amount of the substance. The term also includes situations in which no substance is detected, either because it is not present, or its amount is below the limit of detection of the detection system.

It is generally possible according to the invention to employ all methods suitable for the detection and/or determination of the amount of autoantibodies. Possibilities for carrying out a detection and/or determination of the amount of autoantibodies in the methods of the invention are known to the person skilled in the art.

It is possible in particular to use according to the invention any direct or indirect method for detecting autoantibodies.

In the direct methods, the binding of the autoantibodies to be detected to the tumor-associated antigens or isolated peptides as described above is determined via a change in the chemical or physical properties, so that subsequent detection steps with labelled binding partners are unnecessary.

It is preferred according to the invention for autoantibodies to be detected in an immunoassay, preferably in a solid-phase immunoassay, with direct or indirect coupling of a binding partner. The detection can take place in an ELISA, an RIA or a fluorescence or chemiluminescence immunoassay. The procedure for these detection methods is known to the person skilled in the art.

In an ELISA, for example, antigen (e.g., an isolated peptide according to the present invention) is bound directly or indirectly to a support material such as polystyrene. Incubation with the antibodies to be detected is followed by detection of antigen-bound antibodies directly or indirectly by means of enzyme-coupled substances. These substances may be antibodies, fragments of antibodies or high-affinity ligands. Examples of suitable enzymes are peroxidase, alkaline phosphatase, (3-galactosidase, urease or glucose oxidase. Quantification of the bound antibodies is, for example, possible by adding a chromogenic substrate for the bound enzymes.

In a radioimmunoassay, the antigen is bound directly or indirectly to a support material such as polystyrene. Incubation with the antibodies to be detected is followed by detection of antigen-bound antibodies by means of substances having a radioactive label such as $^{125}I$. These substances may be antibodies, fragments of antibodies or high-affinity ligands. The bound radioactivity can be quantified by means of a suitable measuring instrument.

By the same principle, in a fluorescence immunoassay the antigen-bound antibodies are detected by means of substances which have a fluorescent label such as fluoroscein isothiocyanate (FITC). These substances may be antibodies, fragments of antibodies or high-affinity ligands. The bound amount of fluorescent dye is then quantified by means of a suitable measuring instrument.

Chemiluminescent immunoassays have been shown to be more sensitive than the conventional colorimetric assays, and do not require long incubations or the addition of stopping reagents, as is the case in some colorimetric assays. Among various enzyme assays that employ light-emitting reactions, one of the most successful assays is the enhanced chemiluminescent immunoassay involving a horseradish peroxidase (HRP) labelled antibody or antigen and a mixture of chemiluminescent substrate, hydrogen peroxide, and enhancers.

It is also possible according to the invention to detect antibodies in an agglutination test or gel diffusion test. These detection methods are also known to the person skilled in the art.

In the gel diffusion test, the antigen solutions or antibody solutions are preferably put into neighboring, adjacent wells of agar or agarose plates. If the substances diffuse out of their wells, concentration gradients form, starting from the wells. If the overlapping antigen and antibody concentrations in the gel are within certain proportions, and the antibody solution contains antibodies against the antigen, visible precipitates are formed in the gel.

In the agglutination test, antigen-carrying particles such as particles of latex or polystyrene are crosslinked by antibodies. The aggregates formed can be detected for example by turbodimetry.

According to the present invention, a biological sample may be a tissue sample, including body fluids, and/or a cellular sample and can be obtained in a conventional way, such as by tissue biopsy, including punch biopsy, and removal of blood, bronchial aspirate, sputum, urine, feces or other body fluids. The term "biological sample" also includes according to the invention fractions of biological samples. Particularly preferred biological samples in accordance with the present invention are body fluids, such as blood serum and blood plasma.

A binding agent such as an autoantibody is specific for its target, such as an antigen or an isolated peptide disclosed herein, if it binds thereto. The term "binding" relates according to the invention preferably to a specific binding. "Specific binding" means that a binding to a target such as an epitope for which a binding agent such as an autoantibody is specific is stronger by comparison with the binding to another target. A "stronger binding" can be characterized for example by a lower dissociation constant.

The term "peptide" generally relates to substances which include at least 2, at least 3, at least 4, at least 6, at least 8, at least 10, at least 12 or at least 14 and preferably up to 8, 10, 12, 14, 16, 18, 20, 25, 30, 50, or 100 consecutive amino acids which are connected together by peptide bonds. According to the present invention, preferred peptides consist of 8 to 25, 10 to 20 or 12 to 18 amino acids. Particularly preferred peptides consist of 8 to 25, preferably 10 to 20, more preferably 12 to 18 amino acid residues and comprise at least 8, preferably at least 10, more preferably at least 12 contiguous amino acid residues of an amino acid sequence selected from the group consisting of SEQ ID NOs: 1 to 21. Even more preferred peptides are selected from the group consisting of SEQ ID NOs: 1 to 21. The term "protein" relates to large peptides, preferably peptides having more than 100 amino acids, but the terms "peptide" and "protein" are generally used exchangeably herein. According to the present invention, the peptides or proteins may be modified so as to allow immobilization on a support. For example, the modified peptides or proteins may comprise one or more additional components (such as additional amino acid residues or tags) that facilitate direct or indirect binding to the support material.

The term "support", as used herein, preferably refers to a solid support (also referred to as solid phase). It is possible to use as solid support, for example, any support able to bind to a tumor-associated antigen, isolated peptide and/or antibody. Such supports may comprise support materials such as glass, polystyrene, polypropylene, polyethylene, dextran, nylon, natural or modified celluloses, polyacrylamides, agaroses and magnetite. The support may have any possible structural configuration as long as the molecule bound thereto, such as a tumor-associated antigen, isolated peptide or antibody, is able to bind to its binding partner. Suitable configurations include a spherical configuration (e.g., beads), a cylindrical configuration such as the inside and/or bottom of a test vessel or well, or a flat configuration such as test strips etc.

The proteins and peptides according to the present invention are preferably isolated. The terms "isolated protein" or "isolated peptide" mean that the protein or peptide is separated from its natural environment. An isolated protein or peptide may be in an essentially purified and/or pure state. The term "essentially purified" or "essentially pure" means that the protein or peptide is essentially free of other substances, e.g. substances with which it is present in nature or in vivo.

According to the invention, peptides can be synthetically produced by chemical synthesis methods which are well known in the art, e.g. in a solid or liquid phase. Alternatively, a peptide can be produced in a microorganism which produces the peptide which is then isolated and if desired, further purified. Thus, the peptide can be produced in microorganisms such as bacteria, yeast, or fungi; in a eukaryote cells such as mammalian or insect cells; or, in a recombinant virus vector such as adenovirus, poxvirus, herpesvirus, Simliki forest virus, baculovirus, bacteriophage, sindbis virus, or sendai virus. Suitable bacteria for producing the peptide include *Escherichia coli, Bacillus subtilis*, or any other bacterium that is capable of expressing peptides. Suitable yeast types for expressing the peptide include, but are not limited to *Saccharomyces cerevisiae, Schizosaccharomyces pombe, Candida*, or any other yeast capable of expressing peptides. Methods for using the aforementioned bacteria, recombinant virus vectors, eukaryote cells to produce peptides are well known in the art.

In one embodiment, the peptide merely includes natural amino acids. The term "natural amino acid", as used herein, refers to an amino acid selected from the group consisting of histidine, isoleucine, leucine, lysine, methionine, phenylalanine, threonine, tryptophan, valine, alanine, arginine, asparagine, aspartic acid, cysteine, glutamic acid, glutamine, glycine, proline, serine and tyrosine.

The peptides of the invention may also be modified so as to increase their stability. Such modifications include N-terminal modifications, such as acetylation, C-terminal modifications, such as amidation, incorporation of non-natural amino acids, incorporation of pseudo-peptide bonds and cyclization.

According to the invention, a peptide may include natural amino acids and non-natural amino acids. The term "non-natural amino acid", as used herein, refers to an amino acid having a structure different from those of the 20 natural amino acid species listed above. Since non-natural amino acids have structures similar to those of natural amino acids, non-natural amino acids may be classified as derivatives or analogs of given natural amino acids.

Cyclization results in a cyclic peptide. According to the invention, the term "cyclic peptide" relates to a peptide or polypeptide chain which forms a ring. A peptide can be cyclized in four different ways: head-to-tail (C-terminus to N-terminus), head-to-side chain, side chain-to-tail or side-chain-to-side-chain. Particularly preferred according to the invention are peptides containing two or more residues containing thiol groups such as cysteines which can form intramolecular disulphide bridges giving cyclic peptides.

According to the invention, a peptide may also be covalently or non-covalently bound to one or more other compounds. Such compounds include peptidic compounds such as peptides and proteins as well as non-peptidic compounds such as polyethylene glycol (PEG).

It is to be understood that expressions such as "plurality of isolated peptides" or "at least X isolated peptides", as used herein, refer to a plurality of or to at least X distinct isolated peptides. These distinct isolated peptides may be present in multiple copies.

A nucleic acid is according to the invention preferably deoxyribonucleic acid (DNA) or ribonucleic acid (RNA). Nucleic acids include according to the invention genomic DNA, cDNA, mRNA, recombinantly prepared and chemically synthesized molecules. A nucleic acid may according to the invention be in the form of a single-stranded or double-stranded and linear or covalently circularly closed molecule.

According to the present invention, the nucleic acid may be present in a vector, where appropriate with a promoter which controls the expression of the nucleic acid. The term "vector" is used in this connection in its most general meaning and includes all intermediate vehicles for a nucleic acid which make it possible for example for the nucleic acid to be introduced into prokaryotic and/or into eukaryotic cells and, where appropriate, be integrated into a genome. Such vectors are preferably replicated and/or expressed in the cell. Vectors include plasmids, phagemids, bacteriophages or viral genomes. The term "plasmid" as used herein relates generally to a construct of extrachromosomal genetic material, usually a circular DNA duplex, which can replicate independently of chromosomal DNA. In one embodiment, the vector is an expression vector.

The term "host cell" relates according to the invention to any cell which can be transformed or transfected with an exogenous nucleic acid, preferably DNA or RNA. The term "host cell" includes according to the invention prokaryotic (e.g. *E. coli*) or eukaryotic cells (e.g. mammalian cells, especially human cells, yeast cells and insect cells). Mammalian cells such as human cells, mouse cells, hamster cells, pig cells, goat cells and primate cells are particularly preferred. The cells can be derived from a large number of tissue types and include primary cells and cell lines. Specific examples include keratinocytes, peripheral blood leukocytes, bone marrow stem cells and embryonic stem cells. In further embodiments, the host cell is an antigen-presenting cell, where the term "antigen-presenting cell" includes according to the invention dendritic cells, monocytes and macrophages. A nucleic acid may be present in the host cell in a single or in a plurality of copies and is expressed in one embodiment in the host cell.

According to the invention there is further provided a diagnostic device comprising an isolated peptide as defined above or a panel of isolated peptides as defined above, wherein, preferably, the isolated peptide or panel of isolated peptides is immobilized on a support.

According to the present invention, a diagnostic device can take different forms, and it can be varied depending on the precise nature of the assay being performed. For example, the isolated peptide of the invention may be coated onto a solid support, typically nitrocellulose or other hydrophobic porous material. Alternatively, the peptide may be coated on a synthetic plastics material, multi-well plate, microtitre assay plate, microarray chip, latex bead, filter comprising a cellulosic or synthetic polymeric material, glass or plastic slide, dipstick, capillary fill device and the like. Coating of the peptides to these surfaces can be accomplished by methods known in the art. Protein carriers are typically used for complexing, with BSA or adhesive peptides being the most preferred. In one embodiment, the peptide of the invention is releasably immobilised on the solid support. In a further preferred embodiment, the peptide is non-releasably immobilised on the solid support. In one embodiment, the diagnostic device is a multi-well plate. In one embodiment, the diagnostic device is an enzyme-linked immunosorbent diagnostic device.

In the methods for the diagnosis, prognosis and/or monitoring of cancer in a patient according to the present invention, the presence of cancer or an increased risk of developing cancer is preferably indicated by the presence of the autoantibodies and/or an amount of the autoantibodies which is above a pre-defined cut-off value, wherein the autoantibodies specifically bind to at least one tumor-associated antigen as defined above or to at least one isolated peptide as defined above.

In one embodiment, the term "an amount of autoantibodies which is above a pre-defined cut-off value", as used herein, means that the level of autoantibodies is preferably by at least 5%, by at least 10%, by at least 20%, by at least 30%, by at least 40%, by at least 50%, by at least 60%, by at least 70%, by at least 80%, by at least 90%, by at least 100%, by at least 110%, by at least 120%, by at least 130%, by at least 140%, by at least 150%, by at least 200%, by at least 250%, by at least 300%, by at least 400%, or by at least 500% higher compared to the pre-defined cut-off value.

In preferred embodiments, the methods for the diagnosis, prognosis and/or monitoring of cancer in a patient, in particular the step of detection and/or determination of the amount of autoantibodies, comprise the use of sample-internal blank normalization. Preferably, the term "sample-internal blank normalization", as used herein, refers to the calculation of a quotient of a first signal obtained from the reaction of the sample with a peptide-coated surface and a second signal obtained from the reaction of the same sample with a non-peptide-coated surface (=blank control), wherein, preferably, the term "peptide" refers to an isolated peptide as defined herein and/or the term "surface" refers to the surface of a support as defined herein. For example, a quotient of 2 means that the first signal is twice as high as the second signal.

In one embodiment, the term "pre-defined cut-off value" refers to a quotient of at least 2, preferably at least 3, more preferably at least 4, even more preferably at least 5, even more preferably at least 6, wherein the quotient is calculated as indicated above. In one embodiment, the pre-defined cut-off value is a quotient as defined above which is selected from the group consisting of 2, 3, 4, 5, 6, 7, 8, 9 and 10.

"Prognosis" as used herein refers to a prediction of outcome and, in particular, the probability of progression-free survival (PFS) or disease-free survival (DFS). Survival is usually calculated as an average number of months (or years) that 50% of patients survive, or the percentage of patients that are alive after 1, 5, 15, and 20 years. Prognosis is important for treatment decisions because patients with a good prognosis are usually offered less invasive treatments, while patients with poor prognosis are usually offered more aggressive treatment, such as more extensive chemotherapy drugs.

"Monitoring of cancer" according to the invention preferably comprises detection and/or determination of the amount of autoantibodies in a first sample of a patient at a first point in time and in a further sample of the patient at a second point in time, wherein the regression, progression, course and/or onset of cancer may be determined by comparing the two samples.

An amount of autoantibodies in the further sample at the second point in time which is decreased compared to the amount of autoantibodies in the first sample taken at the first point in time may indicate a regression, a positive course, e.g. a successful treatment, or a reduced risk for an onset of cancer in the patient.

An amount of autoantibodies in the further sample at the second point in time which is increased compared to the amount of autoantibodies in the first sample taken at the first point in time may indicate a progression, a negative course, e.g. an unsuccessful treatment, recurrence or metastatic behavior, an onset or a risk for an onset of cancer in said patient.

By "increased risk of developing cancer" is meant a subject that is identified as having a higher than normal chance of developing cancer, compared to the general population. In addition, a subject who has had, or who currently has cancer, is a subject who has an increased risk for developing cancer, as such a subject may continue to develop cancer. Subjects who currently have, or who have had, cancer also have an increased risk for cancer metastases.

As used herein, the term "kit of parts (in short: kit)" refers to an article of manufacture comprising one or more containers and, optionally, a data carrier. Said one or more containers may be filled with one or more of the above mentioned means or reagents. Additional containers may be included in the kit that contain, e.g., diluents, buffers and further reagents. Said data carrier may be a non-electronical data carrier, e.g., a graphical data carrier such as an information leaflet, an information sheet, a bar code or an access code, or an electronical data carrier such as a floppy disk, a compact disk (CD), a digital versatile disk (DVD), a microchip or another semiconductor-based electronical data carrier. The access code may allow the access to a database, e.g., an internet database, a centralized, or a decentralized database. Said data carrier may comprise instructions for the use of the kit in the methods of the invention. In addition, the data carrier may comprise information or instructions on how to carry out the methods of the present invention.

The term "(therapeutic) treatment", in particular in connection with the treatment of cancer as used herein, relates to any treatment which improves the health status and/or prolongs (increases) the lifespan of a patient. Said treatment may eliminate cancer, reduce the size or the number of tumors in a patient, arrest or slow the development of cancer in a patient, inhibit or slow the development of new cancer in a patient, decrease the frequency or severity of symptoms in a patient, and/or decrease recurrences in a patient who currently has or who previously has had cancer. In one embodiment, the treatment of the cancer comprises one or more selected from the group consisting of surgery (e.g. surgical removal of the primary tumor), chemotherapy, hormonal therapy, radiation therapy and immunotherapy/targeted therapy.

The presence of autoantibodies and/or an amount of autoantibodies which is above a pre-defined cut-off value may indicate the presence of cancer or an increased risk of developing cancer. In consequence thereof, the medical practitioner may choose to administer cancer treatment, such as the one described above.

The methods according to the present invention as well as the isolated peptides, panels of isolated peptides, diagnostic devices and kits disclosed herein facilitate a specificity of at least 97.5%, preferably at least 98%, and a sensitivity of at least 23%, preferably at least 24%. Preferably, these values are achieved in the screening of at least 1000, preferably at least 1400 individuals comprising healthy individuals and individuals having cancer.

The term "specificity", as used herein, relates to the percentage of healthy individuals who are correctly identified as not having cancer. For example, a specificity of 97.5% indicates that there are 2.5% false-positive results, whereas 97.5% of healthy individuals are not tested positively.

The term "sensitivity", as used herein, refers to the percentage of patients having cancer who are correctly identified as having cancer. For example, a sensitivity of 23% indicates that 23% of all cancer patients are identified as such.

Depending on the prevalence of the cancer in the screened population, the methods according to the present invention as well as the isolated peptides, panels of isolated peptides, diagnostic devices and kits disclosed herein facilitate a positive predictive value (PPV) of more than 30%. In one embodiment, the prevalence of the cancer in the screened population is in the range of from 0.5% to 5%, preferably 1% to 3.5%, more preferably 1.5% to 3.5%, more preferably 2% to 3.5%, even more preferably 2.5% to 3.5%.

The present invention is further illustrated by the following examples which are not be construed as limiting the scope of the invention.

EXAMPLES

Example 1: Bead-Based Luminex® Screening of Tumor-Associated Antigen Peptides

A large-scale multistep screening approach using a bead-based multiplexing platform was established to individually analyze overlapping peptides that cover entire tumor-associated antigens (n=50; listed in Table 3) and to detect tumor-associated autoantibodies in lung carcinoma patients. The antigens were identified by comprehensive literature search.

TABLE 3

Tumor-associated antigens used for the screening approach described herein.

| Tumor-associated antigen | Accession-N° |
|---|---|
| Annexin I | P04083 |
| Annexin II | P07355 |
| BAGE | Q29RY1 |
| Beta-Enolase | P13929 |
| BIRC5 | O15392 |
| Cancer-associated gene 1 protein (CAGE-1) | Q8TC20 |
| Cathepsin D | P07339 |
| cDNA FLJ13744 fis | Q9H8D1 |
| CEA-AAA51971-overexpressed | Q13985 |
| c-myc | P01106 |
| Cytokeratin19 | P08727 |
| Dickkopf-related protein 1 | O94907 |
| ELAV-like protein 3 (HuC) | Q14576 |
| ELAV-like protein 4 (HuD) | P26378 |
| Elongation factor 1-alpha 2 | Q05639 |
| Endoplasmin (gp96-homolog) | P14625 |
| Eukaryotic translation initiation factor 4 gamma 1 | Q04637 |
| flk-1 (VEGFR-2) | P35968 |
| GAGE1 | Q13065 |
| GALA_HUMANGalanin | P22466 |
| her2/neu | P04626 |
| HER-4 | Q15303 |
| ICAM1 | P05362 |

TABLE 3-continued

Tumor-associated antigens used for the screening approach described herein.

| Tumor-associated antigen | Accession-N° |
|---|---|
| KKLC1 | Q5H943 |
| K-ras 2 | P01116 |
| MAGE2 | P43356 |
| MAGEA1 | P43355 |
| MAGEA10 | P43363 |
| MAGEA3 | P43357 |
| MAGEA4 | P43358 |
| MAGEB2 | O15479 |
| MAGEC1 | A0PK03 |
| MUC1 | P15941 |
| Mucin-4 | Q99102 |
| Nanog | Q9H9S0 |
| Notch-1 | Q6IAD4 |
| NY-ESO-1-Cancer/testis antigen 1 | P78358 |
| p53-Cellular tumor suppressor antigen | P04637 |
| Placenta-specific protein 1 | Q9HBJ0 |
| Prame/OIP4 | P78395 |
| Secretoglobin family 3A member 2 | Q96PL1 |
| SGT1 | O95905 |
| SOX10 | P56693 |
| SOX2-Transcription factor | P48431 |
| SSX2-Synovial sarcoma | Q16385 |
| SYT-SSX1 fusion protein | A4PIV7 |
| TRIO and F-actin-binding protein | Q9H2D6 |
| Ubiquitin carboxyl-terminal hydrolase isozyme L1 | P09936 |
| VEGFA | P15692 |
| XAGE-1 | Q9HD64 |

For inclusion of all possible epitopes, 15-mer peptides were synthesized with an overlap of 11 amino acids (offset of 4 amino acids) resulting in a total of 5735 peptides covering the proteins listed in Table 3. These peptides were exposed to plasma samples from lung carcinoma patients and healthy donors for autoantibody binding. Peptides containing epitopes for tumor-associated autoantibodies generate specific signals in immunoassays and are detectable in plasma samples from lung carcinoma patients but are absent in samples from healthy donors.

The peptide selection procedure led to the identification of a highly specific peptide panel (n=21; disclosed in Table 4) derived from nine different tumor-associated antigens. This carefully selected panel, preferably in combination with a normalization strategy described further below, facilitates a specificity of 98-99% and a positive predictive value (PPV) of >30%. These values outperform currently known performance data (see Table 1).

TABLE 4

Exemplary panel of twenty-one 15-mer peptides derived from nine different tumor-associated antigens warranting maximal specificity, sensitivity and positive predictive values.

| SEQ ID NO. | Sequence | Name | Accession-No |
|---|---|---|---|
| 1 | GPGGPGIPDGPGGNA | Autoimmunogenic cancer/testis antigen NY-ESO-1 | P78358 |
| 2 | GGSTGDADGPGGPGI | Autoimmunogenic cancer/testis antigen NY-ESO-1 | P78358 |
| 3 | AMPFATPMEAELARR | Autoimmunogenic cancer/testis antigen NY-ESO-1 | P78358 |
| 4 | GDADGPGGPGIPDGP | Autoimmunogenic cancer/testis antigen NY-ESO-1 | P78358 |
| 5 | GGGAPRGPHGGAASG | Autoimmunogenic cancer/testis antigen NY-ESO-1 | P78358 |
| 6 | ATPMEAELARRSLAQ | Autoimmunogenic cancer/testis antigen NY-ESO-1 | P78358 |

TABLE 4-continued

Exemplary panel of twenty-one 15-mer peptides derived from nine different tumor-associated antigens warranting maximal specificity, sensitivity and positive predictive values.

| SEQ ID NO. | Sequence | Name | Accession-No |
|---|---|---|---|
| 7 | PRGAGAARASGPGGG | Autoimmunogenic cancer/testis antigen NY-ESO-1 | P78358 |
| 8 | PGIPDGPGGNAGGPG | Autoimmunogenic cancer/testis antigen NY-ESO-1 | P78358 |
| 9 | MQAEGRGTGGSTGDA | Autoimmunogenic cancer/testis antigen NY-ESO-1 | P78358 |
| 10 | PRGPHGGAASGLNGC | Autoimmunogenic cancer/testis antigen NY-ESO-1 | P78358 |
| 11 | LRKKGEPHHELPPGS | Cellular tumor antigen p53 | P04637 |
| 12 | LSPDDIEQWFTEDPG | Cellular tumor antigen p53 | P04637 |
| 13 | MEEPQSDPSVEPPLS | Cellular tumor antigen p53 | P04637 |
| 14 | SVTCTYSPALNKMFC | Cellular tumor antigen p53 | P04637 |
| 15 | CALVASQYGWSGNME | Endoplasmin (gp96-homolog, Tumor rejection antigen 1) | P14625 |
| 16 | EDSYRKQVVIDGETC | GTPase KRas | P01116 |
| 17 | SSSSPLVLGTLEEVP | Melanoma-associated antigen 1 | P43355 |
| 18 | YPLWSQSYEDSSNQE | Melanoma-associated antigen 3 | P43357 |
| 19 | SSSSPLVPGTLEEVP | Melanoma-associated antigen 4 | P43358 |
| 20 | AGAFQAQDEGRSQQP | TRIO and F-actin-binding protein | Q9H2D6 |
| 21 | EHCKMPEAGEEQPQV | XAGE-1 | Q9HD64 |

Figure 2:
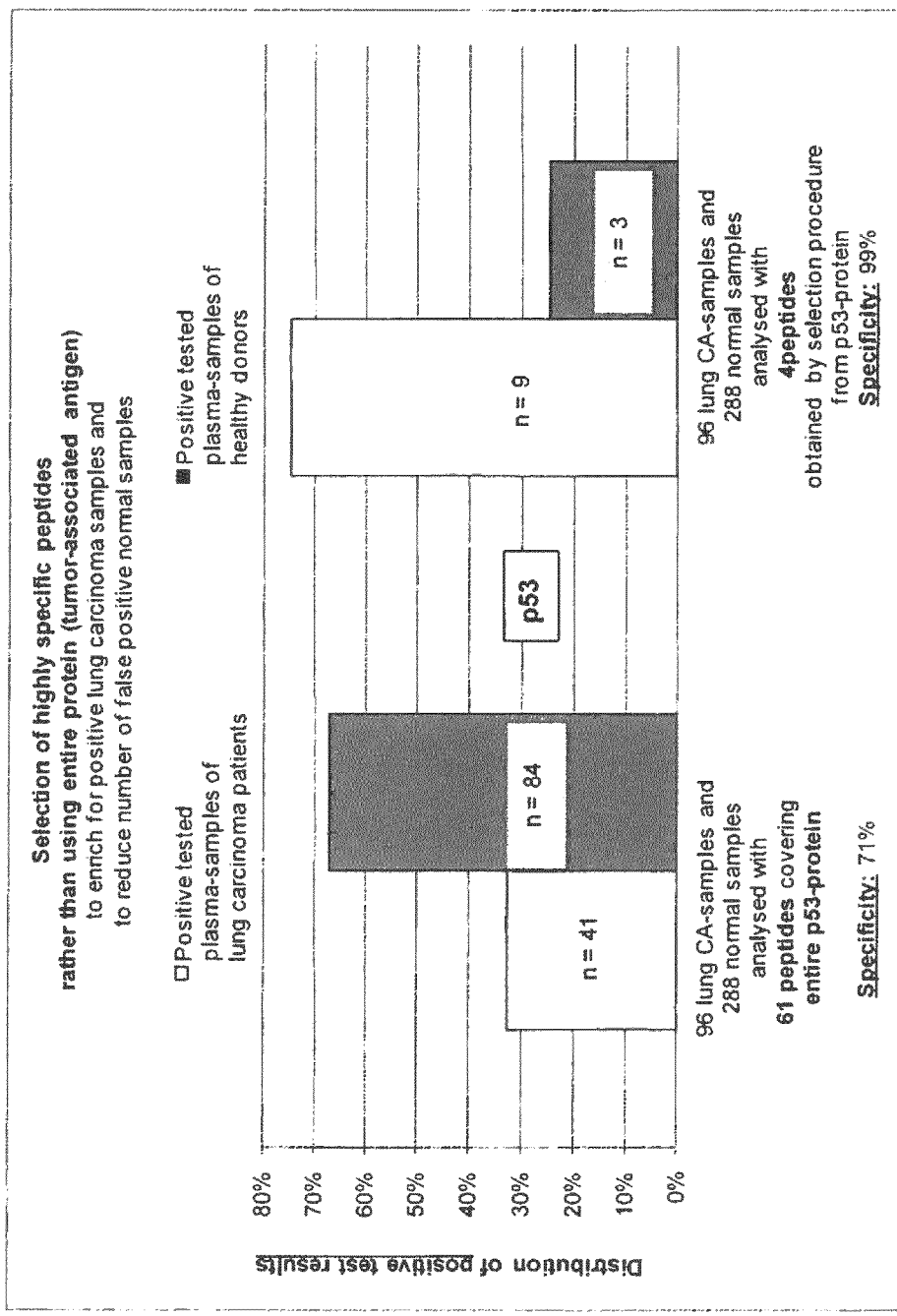
FIG. 2 shows a comparison of an assay using selected p53 peptides and an assay using peptides covering the entire p53 protein sequence in terms of their specificity.
Figure 3:
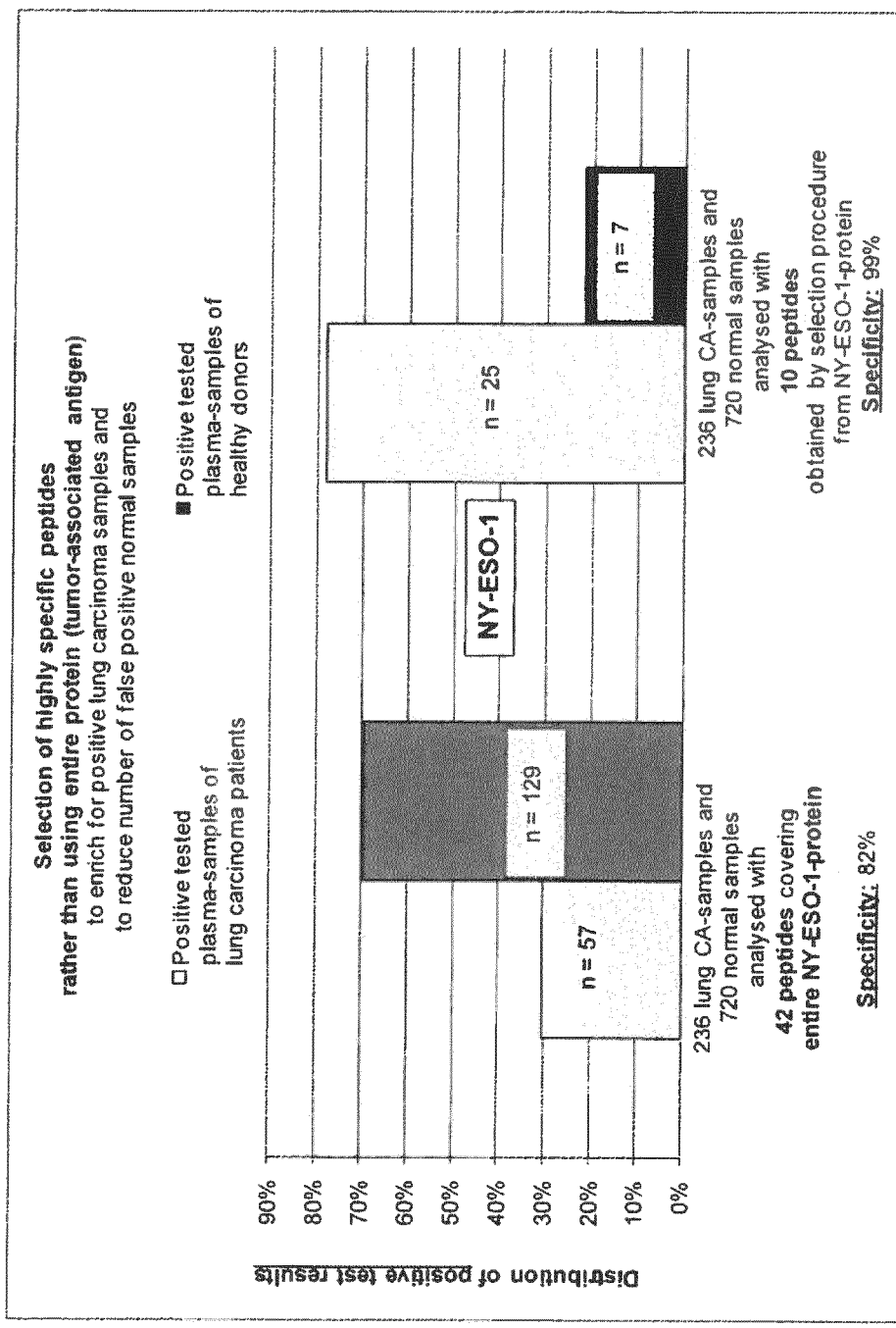
FIG. 3 shows a comparison of an assay using selected NY-ESO-1 peptides and an assay using peptides covering the entire NY-ESO-1 protein sequence in terms of their specificity.

Using individual peptides for the screening of blood samples instead of entire proteins facilitates high specificity because non-specific sequences of a tumor-associated antigen that may cause non-tumor-related binding of antibodies in healthy donors can be excluded during the peptide selection procedure (described in the section "Materials and Methods"). This can be demonstrated by comparing the positive signals obtained with the selected peptides (Table 4) with the positive signals obtained with all peptides derived from a certain tumor-associated antigen (which mimics the usage of the entire protein). As can be seen in FIGS. 2 and 3 as well as in Table 5, positive signal distribution between plasma samples from lung carcinoma patients and plasma samples from healthy donors is significantly worse and, therefore, much lower specificities are achieved, if peptides covering the entire tumor-associated antigen are used instead of selected peptides.

TABLE 5

Comparison of selected peptides and peptides covering entire proteins in terms of their specificity.

| Analyzed screening step | Number of analyzed plasma samples | | Tumor-associated antigen | Peptides covering entire protein (A) Selected peptides (B) | Number of peptides | Distribution of positive test results | | Specificity |
| | Lung carcinoma patients | Healthy donors | | | | Lung carcinoma patients | Healthy donors | |
|---|---|---|---|---|---|---|---|---|
| Primary Screening* | 96 | 288 | p53 | A | 61 | 32.8% n = 41 | 67.2% n = 84 | 71% |
| | | | | B | 4 | 75.0% n = 9 | 25.0% n = 3 | 99% |
| | | | K-Ras 2 | A | 37 | 31.1% n = 19 | 68.9% n = 42 | 85% |
| | | | | B | 1 | 100.0% n = 1 | 0.0% n = 0 | 100% |
| | | | MAGE-1 | A | 55 | 39.8% n = 33 | 60.2% n = 50 | 83% |
| | | | | B | 1 | 100.0% n = 1 | 0.0% n = 0 | 100% |
| | | | MAGE-3 | A | 55 | 30.9% n = 30 | 69.1% n = 67 | 87% |
| | | | | B | 1 | 100.0% n = 2 | 0.0% n = 0 | 100% |

TABLE 5-continued

Comparison of selected peptides and peptides covering entire proteins in terms of their specificity.

| Analyzed screening step | Number of analyzed plasma samples | | | Peptides covering entire protein (A) Selected peptides (B) | Number of peptides | Distribution of positive test results | | Specificity |
|---|---|---|---|---|---|---|---|---|
| | Lung carcinoma patients | Healthy donors | Tumor-associated antigen | | | Lung carcinoma patients | Healthy donors | |
| Secondary Screening* | 236 | 720 | MAGE-4 | A | 67 | 33.3% n = 51 | 66.7% n = 102 | 65% |
| | | | | B | 1 | 100.0% n = 3 | 0.0% n = 0 | 100% |
| | | | TRIO and F-actin-binding protein | A | 540 | 26.2% n = 92 | 73.8% n = 259 | 10% |
| | | | | B | 1 | 100.0% n = 1 | 0.0% n = 0 | 100% |
| | | | NY-ESO-1 | A | 42 | 30.6% n = 57 | 69.4% n = 129 | 82% |
| | | | | B | 10 | 78.1% n = 25 | 21.9% n = 7 | 99% |
| | | | Endoplasmin | A** | 20 | 39.5% n = 62 | 60.5% n = 95 | 87% |
| | | | | B | 1 | 85.7% n = 6 | 14.3% n = 1 | 99% |

*The multistep screening approach is described in section "Materials and Methods".
**In case of Endoplasmin, peptides do not cover entire protein.

Figure 4:
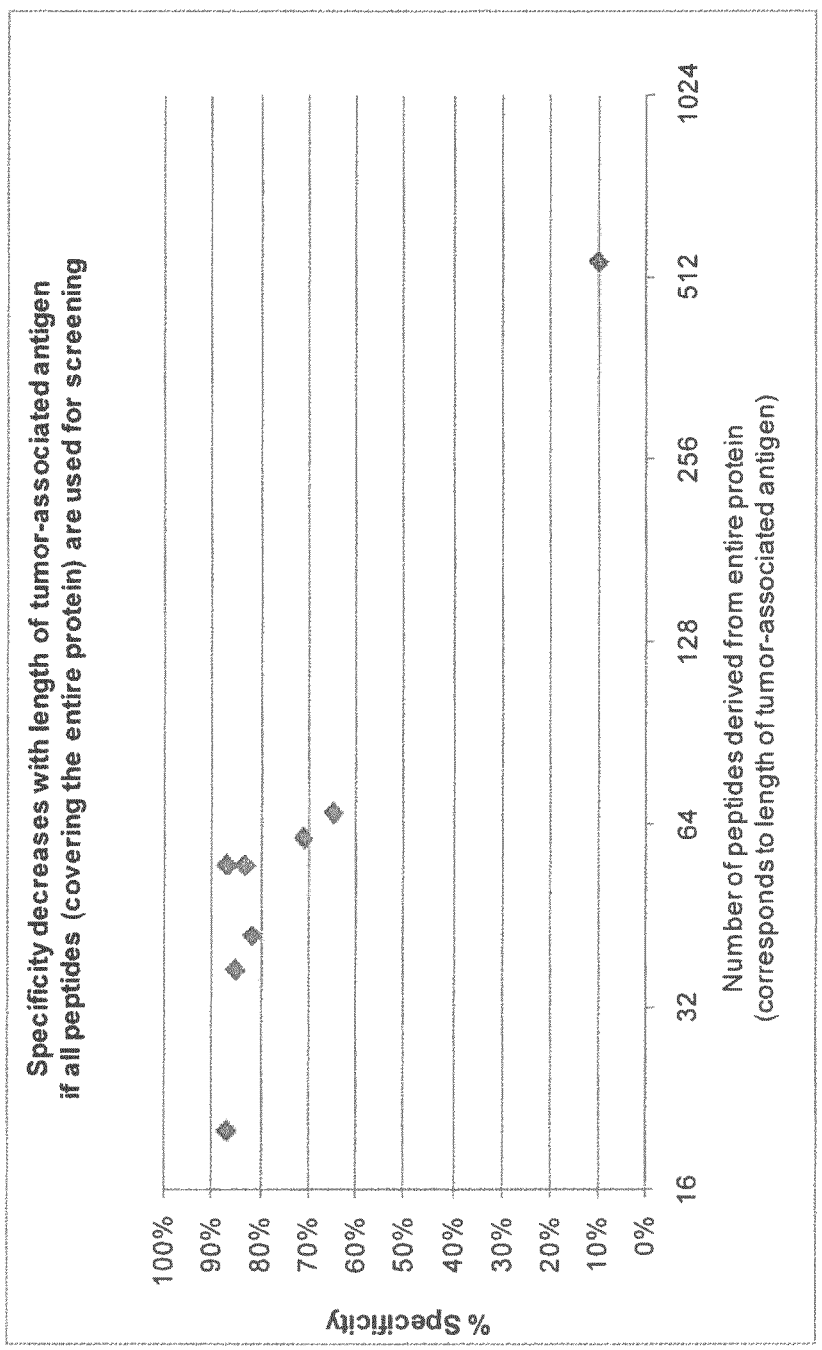
FIG. 4 shows the correlation between protein size (number of overlapping peptides) and specificity.

The decrease of specificity correlates with the length of the respective protein which corresponds to the number of overlapping peptides that cover the entire protein (FIG. 4 and Table 6). This is due to the fact that the probability of non-tumor-associated binding sites increases with the size of the protein.

TABLE 6

Correlation between protein size (number of overlapping peptides) and specificity.

| Tumor-associated antigen | Peptides covering entire protein | | Selected peptides | |
|---|---|---|---|---|
| | Number of peptides* | Specificity | Number of peptides | Specificity |
| p53 | 61 | 71% | 4 | 99% |
| K-Ras 2 | 37 | 85% | 1 | 100% |
| MAGE-1 | 55 | 83% | 1 | 100% |
| MAGE-3 | 55 | 87% | 1 | 100% |
| MAGE-4 | 67 | 65% | 1 | 100% |
| TRIO and F-actin-binding protein | 540 | 10% | 1 | 100% |
| NY-ESO-1 | 42 | 82% | 10 | 99% |
| Endoplasmin** | 20 | 87% | 1 | 99% |

*Some peptides are not included due to failed peptide synthesis. Redundant peptide sequences are removed.
**In case of Endoplasmin, peptides do not cover entire protein.

For example, 113 of 398 (28%) plasma samples of lung carcinoma patients were tested positive using the 21 selected peptides listed in Table 4. In order to show contribution of the different peptides to total sensitivity, the peptides were separated in three groups (see FIG. 5 and Table 7a):

Group 1: 10 peptides obtained from NY-ESO-1

Group 2: 4 peptides obtained from p53

Group 3: 7 peptides obtained from 7 additional proteins (1 peptide each)

K-Ras 2

Endoplasmin

TRIO and F-actin-binding protein

MAGE-1, MAGE-3, MAGE-4 antigens

XAGE-1

By using these peptides, high sensitivity is achieved without loss of specificity (≥97.5% in >1000 samples derived from healthy donors). One fraction of plasma samples from lung carcinoma patients is tested positive with peptides derived from NY-ESO-1, a second fraction with peptides derived from p53 and a third fraction with peptides derived from above listed additional tumor-associated antigens. The number of plasma samples from lung carcinoma patients tested positive with peptides from different groups is relatively low which demonstrates low redundancy of the selected peptides (see also Table 7a).

TABLE 7a

Contribution of selected peptides (as listed in Table 4) to total sensitivity.
Exemplary distribution of positive test results (a total of 113 lung carcinoma samples)

| | Non-redundancy (tumor samples are detected by one antigen only) | | |
|---|---|---|---|
| Peptides derived from | | Number of lung carcinoma samples | |
| NY-ESO-1 | | 48 | 95 |
| p53 | | 28 | |
| MAGE-1/3/4 | 4 | | 19 |

TABLE 7a-continued

Contribution of selected peptides (as listed in Table 4) to total sensitivity.
Exemplary distribution of positive test results (a total of 113 lung carcinoma samples)

| | |
|---|---|
| Endoplasmin | 4 |
| K-Ras 2 | 0 |
| TRIO and F-actin-binding protein | 1 |
| XAGE-1 | 10 |

Redundancy (number of lung carcinoma samples detected by peptides derived from two antigens)

| Peptides derived from | NY-ESO-1 | p53 | MAGE-1/3/4 | Endo-plasmin | K-Ras 2 | TRIO and F-actin-binding protein | XAGE-1 | Total |
|---|---|---|---|---|---|---|---|---|
| NY-ESO-1 | | 7 | 3 | 0 | 0 | 0 | 3 | 17 |
| p53 | | | 2 | 0 | 0 | 0 | 2 | |
| MAGE-1/3/4 | | | | 0 | 0 | 0 | 0 | |
| Endoplasmin | | | | | 0 | 0 | 0 | |
| K-Ras 2 | | | | | | 0 | 0 | |
| TRIO and F-actin-binding protein | | | | | | | 0 | |
| XAGE-1 | | | | | | | | |

Redundancy (one sample is detected by three antigens)

| | |
|---|---|
| 1 lung carcinoma sample is detected by peptides derived from p53, MAGE-1/3/4 and XAGE-1 | 1 |

In Table 7b, the individual peptides as listed in Table 4 are ranked according to their ratio of reactivities in a lung carcinoma group (n=384) and the healthy donor group (n=2953). The more reactivities in the lung carcinoma group and the less reactivities in the normal donor group, the better the rank. For example, the best peptide (rank 1) detects 15 lung carcinoma samples without creating any positive result in the normal donor group, resulting in a sensitivity of 3.9% and a specificity of 100%. By adding the marker peptides of ranks 2-5 to the panel, sensitivity accumulates to 11.5% (specificity=99.8%). Additional lung carcinomas are detected by adding the marker peptides of ranks 6-15 (sensitivity accumulates to 23.2%, maintaining a high specificity of 98.8%). When adding marker peptides of ranks 16-20 to the panel, a further improvement of sensitivity is achieved (accumulation to 24.1%) with only a minor loss of specificity (98.5%).

TABLE 7b

Ranking of the defined marker peptides according to observed reactivities in the tumor group versus the normal group (smokers and non-smokers, marker peptides 1-21 including XAGE-1)

| Antigen | Sequence of peptide | Number of reactivities in a pool of 384 lung carncinoma samples (LC) | Number of reactivities in a pool of 2953 normal donor samples (ND) | Ranking according to ratio LC/ND | Accumulated Sensitivity | Accumulated Specificity |
|---|---|---|---|---|---|---|
| NY-ESO-1 | GPGGPGIPDGPGGNA | 15 | 0 | 1 | 3.9% | 100.0% |
| XAGE-1 | EHCKMPEAGEEQPQV | 19 | 2 | 2 | 8.3% | 99.9% |
| NY-ESO-1 | AMPFATPMEAELARR | 9 | 1 | 3 | 9.6% | 99.9% |
| NY-ESO-1 | GGSTGDADGPGGPGI | 14 | 2 | 4 | 10.7% | 99.8% |
| NY-ESO-1 | GDADGPGGPGIPDGP | 19 | 3 | 5 | 11.5% | 99.8% |
| NY-ESO-1 | PRGPHGGAASGLNGC | 5 | 1 | 6 | 12.0% | 99.8% |
| NY-ESO-1 | ATPMEAELARRSLAQ | 28 | 8 | 7 | 14.3% | 99.5% |
| NY-ESO-1 | PGIPDGPGGNAGGPG | 13 | 4 | 8 | 15.4% | 99.4% |
| p53 | LSPDDIEQWFTEDPG | 27 | 10 | 9 | 21.1% | 99.1% |
| p53 | MEEPQSDPSVEPPLS | 2 | 0 | 10 | 21.1% | 99.1% |
| MAGEA1 | SSSSPLVLGTLEEVP | 2 | 0 | 11 | 21.4% | 99.1% |
| K-ras | EDSYRKQVVIDGETC | 2 | 0 | 12 | 21.4% | 99.1% |

TABLE 7b-continued

Ranking of the defined marker peptides according to observed reactivities in the tumor group versus the normal group (smokers and non-smokers, marker peptides 1-21 including XAGE-1)

| Antigen | Sequence of peptide | Number of reactivities in a pool of 384 lung carncinoma samples (LC) | Number of reactivities in a pool of 2953 normal donor samples (ND) | Ranking according to ratio LC/ND | Accumulated Sensitivity | Accumulated Specificity |
|---|---|---|---|---|---|---|
| NY-ESO-1 | PRGAGAARASGPGGG | 10 | 5 | 13 | 21.4% | 98.9% |
| Endoplasmin | CALVASQYGWSGNME | 4 | 2 | 14 | 22.1% | 98.9% |
| MAGEA3 | YPLWSQSYEDSSNQE | 4 | 2 | 15 | 23.2% | 98.8% |
| NY-ESO-1 | GGGAPRGPHGGAASG | 6 | 3 | 16 | 23.2% | 98.7% |
| p53 | LRKKGEPHHELPPGS | 4 | 2 | 17 | 23.2% | 98.7% |
| p53 | SVTCTYSPALNKMFC | 12 | 7 | 18 | 23.7% | 98.5% |
| TRIO | AGAFQAQDEGRSQQP | 1 | 0 | 19 | 24.1% | 98.5% |
| NY-ESO-1 | MQAEGRGTGGSTGDA | 1 | 0 | 20 | 24.1% | 98.5% |
| MAGE-4 | SSSSPLVPGTLEEVP | 0 | 0 | 21 | 24.1% | 98.5% |

More data (larger sample cohorts) are available with marker peptides 1-20 (without XAGE-1-peptide). The ranking of these markers within this sample cohort as well as the accumulated sensitivities and specificities are shown in Table 7c. These data indicate that the ranking of the marker peptides vary with different sample cohorts but similar performance values are achieved (specificity is maintained, sensitivity is slightly increased by adding the XAGE-1-peptide as additional biomarker).

TABLE 7c

Ranking of the defined marker peptides according to observed reactivities in the tumor group versus the normal group (smokers and non-smokers. marker peptides 1-20 without XAGE-1)

| Antigen | Sequence of peptide | Number of reactivities in a pool of 720 lung carncinoma samples (LC) | Number of reactivities in a pool of 3289 normal donor samples (ND) | Ranking according to ratio LC/ND | Accumulated Sensitivity | Accumulated Specificity |
|---|---|---|---|---|---|---|
| NY-ESO-1 | GPGGPGIPDGPGGNA | 31 | 0 | 1 | 4.3% | 100.0% |
| NY-ESO-1 | GGSTGDADGPGGPGI | 30 | 2 | 2 | 6.0% | 99.9% |
| NY-ESO-1 | AMPFATPMEAELARR | 28 | 2 | 3 | 7.6% | 99.9% |
| NY-ESO-1 | GDADGPGGPGIPDGP | 42 | 4 | 4 | 8.6% | 99.8% |
| p53 | LRKKGEPHHELPPGS | 15 | 2 | 5 | 10.6% | 99.8% |
| p53 | MEEPQSDPSVEPPLS | 7 | 0 | 6 | 11.0% | 99.8% |
| MAGE-1 | SSSSPLVLGTLEEVP | 5 | 0 | 7 | 11.7% | 99.8% |
| MAGE-4 | SSSSPLVPGTLEEVP | 5 | 0 | 8 | 11.8% | 99.8% |
| MAGE-3 | YPLWSQSYEDSSNQE | 9 | 2 | 9 | 12.9% | 99.7% |

TABLE 7c-continued

Ranking of the defined marker peptides according to observed reactivities in the tumor group versus the normal group (smokers and non-smokers. marker peptides 1-20 without XAGE-1)

| Antigen | Sequence of peptide | Number of reactivities in a pool of 720 lung carncinoma samples (LC) | Number of reactivities in a pool of 3289 normal donor samples (ND) | Ranking according to ratio LC/ND | Accumulated Sensitivity | Accumulated Specificity |
|---|---|---|---|---|---|---|
| NY-ESO-1 | MQAEGRGTGGSTGDA | 4 | 0 | 10 | 12.9% | 99.7% |
| NY-ESO-1 | PRGPHGGAASGLNGC | 8 | 2 | 11 | 13.2% | 99.7% |
| NY-ESO-1 | GGGAPRGPHGGAASG | 12 | 3 | 12 | 13.3% | 99.6% |
| Endoplasmin | CALVASQYGWSGNME | 7 | 2 | 13 | 14.0% | 99.5% |
| NY-ESO-1 | ATPMEAELARRSLAQ | 61 | 18 | 14 | 16.0% | 99.1% |
| NY-ESO-1 | PRGAGAARASGPGGG | 20 | 6 | 15 | 16.1% | 98.9% |
| p53 | LSPDDIEQWFTEDPG | 64 | 20 | 16 | 21.8% | 98.3% |
| TRIO | AGAFQAQDEGRSQQP | 3 | 0 | 17 | 22.2% | 98.3% |
| K-ras | EDSYRKQVVIDGETC | 3 | 0 | 18 | 22.5% | 98.3% |
| NY-ESO-1 | PGIPDGPGGNAGGPG | 29 | 10 | 19 | 23.2% | 98.0% |
| p53 | SVTCTYSPALNKMFC | 29 | 12 | 20 | 23.8% | 97.6% |

An overview of the performance data in different sample cohorts is given in Table 7d (comparing different sub-cohorts "Smokers & non-smokers" versus "Only smokers") dependent on whether the XAGE-1 biomarker is added to the panel or not (fewer samples were analyzed with the XAGE-1-peptide).

TABLE 7d

Overview of performance data dependent on whether smokers and non-smokers or only smokers are analyzed with and without XAGE-1-peptide as additional biomarker

Figure 5:
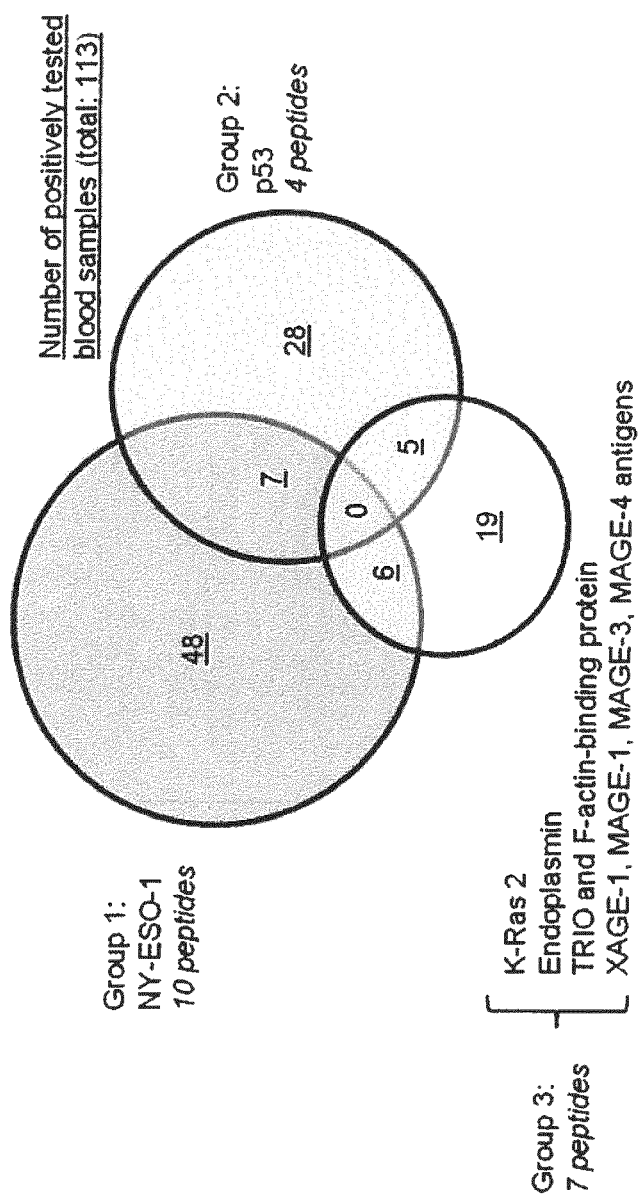
FIG. 5 shows the contribution of selected peptides (listed in Table 4) to total sensitivity. Overlaps indicate redundancies (blood samples are tested positive by peptides of different groups). 113 samples were tested positively in total.
Figure 8:
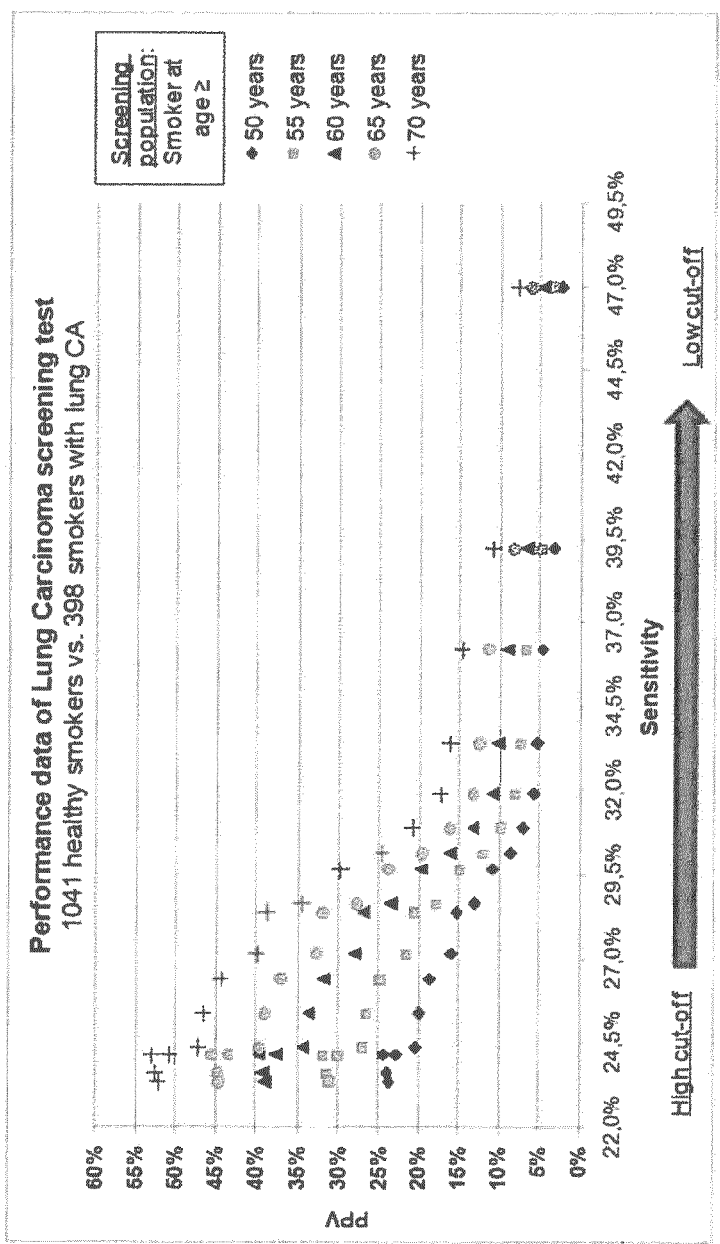
FIG. 8 shows the performance characteristics (sensitivity and PPV) of an exemplary lung cancer screening test as a function of the chosen screening population (age group of smokers) and selected cut-off.

| Biomarker-panel | Cohort | Method | Specificity | Sensitivity | Number of measured plasma samples from lung carcinoma patients (LC) | Number of measured plasma samples from normal donors (ND) | Table/FIG. |
|---|---|---|---|---|---|---|---|
| 20 peptides (without XAGE-1) | Smokers & non-smokers | Luminex ® | 97.6% | 23.8% | 720 | 3289 | Table 7c |
| | Only smokers | ELISA | 97.9% | 26.0% | 450 | 2672 | Not shown |
| 21 peptides (including XAGE-1) | Smokers & non-smokers | Luminex ® | 98.5% | 24.1% | 384 | 2953 | Table 7b |
| | Only smokers | ELISA | 97.8% | 28.4% | 398 | 1041 | Table 7a & 8a FIG. 5 & 8 |

Table 8a shows that all types of lung cancers are detected by the described peptide marker panel (albeit a slightly greater sensitivity in squamous cell carcinoma and slightly lower sensitivity in small cell lung carcinoma are observed). Moreover, early tumor stages are detected (26% sensitivity of stage I). This is important due to the fact that overall cure and survival rates are best at very early stages. Finally, sensitivity is neither dependent on the age nor on the gender of patients.

TABLE 8a

Statistical information about 398 analyzed lung carcinoma samples: gender, tumor type, tumor grading, age distribution. Stated sensitivities are achieved by using the peptide marker panel listed in Table 4.

| | Lung CA-samples | | | |
|---|---|---|---|---|
| Grading | All | Positives | Sensitivity | |
| Ia | 49 | 9 | 18.4% | 25.5% |
| Ib | 101 | 30 | 29.7% | |

TABLE 8a-continued

Statistical information about 398 analyzed lung carcinoma samples: gender, tumor type, tumor grading, age distribution. Stated sensitivities are achieved by using the peptide marker panel listed in Table 4.

| | | | | |
|---|---|---|---|---|
| I ? | 3 | 0 | | |
| IIa | 44 | 13 | 29.5% | 27.1% |
| IIb | 38 | 10 | 26.3% | |
| II ? | 3 | 0 | | |
| IIIa | 63 | 24 | 38.1% | 33.3% |
| IIIb | 18 | 3 | 16.7% | |
| III ? | 6 | 2 | 33.3% | |
| IV | 23 | 8 | 34.8% | 34.8% |
| Unknown | 50 | 14 | 28.0% | 28.0% |
| All | 398 | 113 | 28.4% | |

| | Lung CA-samples | | |
|---|---|---|---|
| Age | All | Positives | Sensitivity |
| <50 | 30 | 9 | 30.0% |
| 50-54 | 51 | 14 | 27.5% |
| 55-59 | 64 | 21 | 32.8% |
| 60-64 | 60 | 12 | 20.0% |
| 65-69 | 49 | 12 | 24.5% |
| ≥70 | 55 | 19 | 34.5% |
| Unknown | 89 | 26 | 29.2% |
| All | 398 | 113 | 28.4% |

| | Lung CA-samples | | | |
|---|---|---|---|---|
| Gender | All | % | Positives | Sensitivity |
| Men | 324 | 81.4% | 87 | 26.9% |
| Women | 74 | 18.6% | 26 | 35.1% |
| All | 398 | 100% | 113 | 28.4% |

| | Lung CA-samples | | | |
|---|---|---|---|---|
| Subtype | All | % | Positives | Sensitivity |
| Squamous cell carcinoma | 123 | 30.9% | 40 | 32.5% |
| Adenocarcinoma | 101 | 25.4% | 23 | 22.8% |
| Large cell carcinoma | 7 | 1.8% | 2 | 28.6% |
| NSCLC (no subtype known) | 87 | 21.9% | 30 | 34.5% |
| SCLC | 64 | 16.1% | 14 | 21.9% |
| Not defined | 16 | 4.0% | 4 | 25.0% |
| All | 398 | 100% | 113 | 28.4% |

Table 8b shows that other lung diseases like COPD, asthma and bronchitis are not tested positive (98-100% specificity) by the described peptide panel. This is important due to the fact that smokers as the target screening population often suffer from such lung diseases.

As expected, other cancer types like colon, gastric, breast, and prostate cancer as well as melanoma show some overlap with lung cancer regarding their tumor-associated autoantibody profile, resulting in a sensitivity of 6-14% with the described peptide panel (Table 8b). This implies that the marker peptide panels need to be further optimized in order to achieve higher sensitivities in these cancer entities.

TABLE 8b

Results of cross-validation using peptide-panel listed in Table 4.

| | Lung disease | | |
|---|---|---|---|
| | Asthma | Bronchitis | COPD |
| Total | 260 | 180 | 38 |
| Positive | 1 | 4 | 0 |
| Negative | 259 | 176 | 38 |
| Specificity | 99.60% | 97.80% | 100.00% |

| | Other cancers | | | | |
|---|---|---|---|---|---|
| | Breast | Colon | Gastric | Melanoma | Prostate |
| Total | 96 | 96 | 70 | 96 | 96 |
| Positive | 6 | 10 | 10 | 6 | 9 |
| Negative | 90 | 86 | 60 | 90 | 87 |
| Sensitivity | 6.30% | 10.40% | 14.30% | 6.30% | 9.40% |

Example 2: Enzyme-Linked Immunosorbent Assay (ELISA)

In order to confirm the results of the bead-based screening platform, a second immunological detection system was established. For this purpose, the enzyme-linked immunosorbent assay (ELISA) format was used as the preferred in vitro diagnostic tool in clinical laboratories.

Concordance analysis of both immunoassays (bead-based Luminex® assay versus ELISA with peptide-coated immunoplates) revealed a concordance rate of 93% regarding the test results "positive" or "negative" for tumor-associated antibodies (Table 9; see below section "Materials and Methods" for the description of cut-off values and definition of test results).

TABLE 9

Concordance of test results (positive/negative) when comparing Luminex ® data and ELISA data.

Defined peptide-panel of Table 4 is sub-divided in 3 groups:

| Group 1: | 10 peptides derived from NY-ESO-1-protein |
| Group 2: | 4 peptides derived from p53-protein |
| Group 3: | 7 peptides derived from MAGE-antigens, K-ras 2, Endoplasmin, TRIO and F-actin binding protein, XAGE-1 |

Concordance of test results (positive/negative) when comparing Luminex ® data and ELISA data

| Samples obtained from | Peptides obtained from | Concordance | Mean | Total mean |
|---|---|---|---|---|
| Healthy donors | Group 1 | 88% (42/48) | 94% | 93% |
| | Group 2 | 94% (45/48) | | |
| | Group 3 | 100% (48/48) | | |
| Lung carcinoma patients | Group 1 | 85% (41/48) | 92% | |
| | Group 2 | 96% (46/48) | | |
| | Group 3 | 94% (45/48) | | |

Using optimized assay parameters and background normalization as described in the section "Materials and Methods", a specificity of 99% and a sensitivity of 24% was achieved resulting in a PPV of 40% and a NPV of 98% (assuming a screened risk population of smokers with a prevalence for lung cancer of 2.8%).

The results were obtained after analyzing a large number of plasma samples obtained from lung carcinoma patients (n=398) and plasma samples obtained from healthy donors (n=1041). The number of samples used for validation in the present invention significantly exceeds the number usually stated in publications (see Table 1). The large number of samples used for validation warrants representative and reliable data and therefore applicability in clinical routine screening.

MATERIALS AND METHODS

Figure 6:
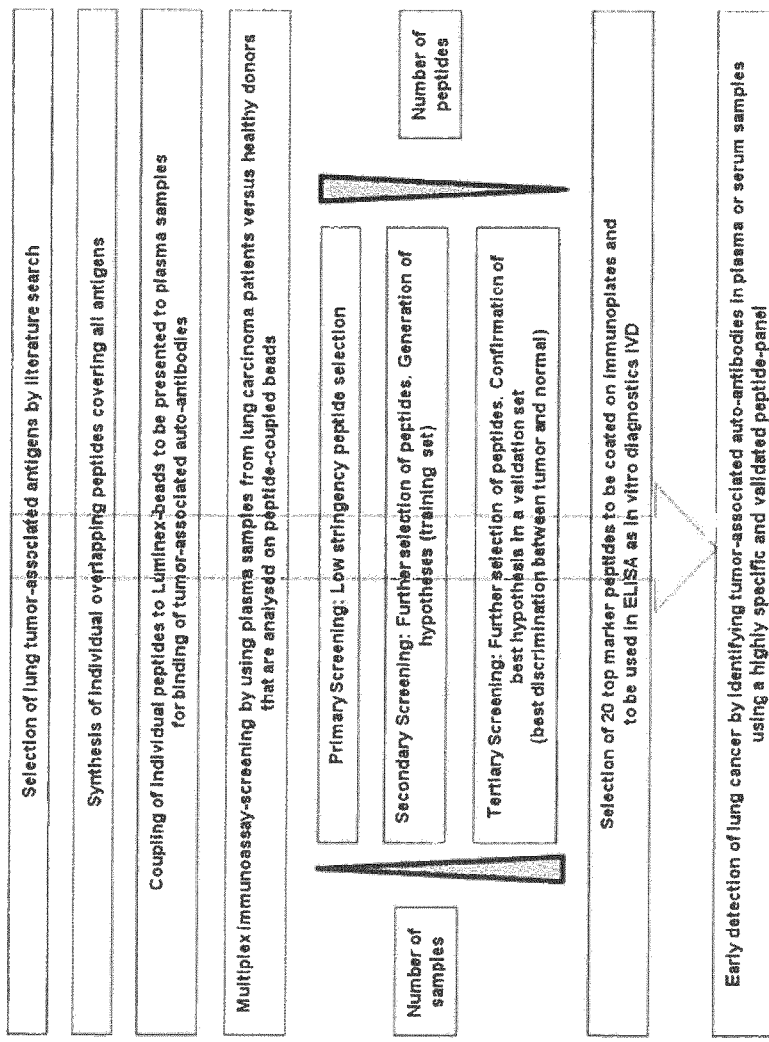
FIG. 6 is a general overview of the multistep screening approach using bead-based Luminex® technology and subsequent validation by ELISA.

A general overview of the multistep screening approach using bead-based Luminex® technology and subsequent validation by ELISA is given in FIG. 6.

A. Selection of tumor-associated antigens and peptide synthesis

Peptides were synthesized and individually analyzed using the bead-based Luminex® system (see below) by presenting these peptides to plasma samples from lung carcinoma patients in comparison to plasma samples from healthy donors.

In order to analyze the whole proteins of the 50 tumor-associated antigens listed in Table 3 and to include all possible epitopes, 15-mer peptides were used with an overlap of 11 amino acids (offset of 4 amino acids) resulting in a total of 5735 peptides.

B. Screening approach using the bead-based Luminex® system for mulitplex immunological assays Overview: The peptides described above were synthesized, N-terminally biotinylated and coupled to avidin-coated Luminex® beads (LumAvidin® beads, Luminex Corp.). A total of 96 bead colors (96 "regions") could be analyzed simultaneously. Each bead region was coupled with one peptide sequence. Therefore, 96 sequences were analyzed simultaneously in an immunological multiplexing assay.

Coupling reaction: In this step, biotinylated peptides are coupled to avidin-coupled beads. It is important to define and document which region corresponds to which peptide.

Resuspend LumAvidin® beads by vortexing and transfer 120 µl (=300,000 beads) into 96-well filter plate (Pall): 1 bead region per well=96 regions.

Add 50 µl reaction buffer (0.1% BSA in 1×PBS, pH 7.5) per well.

Vacuum-filtrate filter plate for 5 seconds (beads remain in wells).

Add 192 µl reaction buffer and 8 µl peptide (40 ng/µl in 0.8% DMSO in water).

Incubate for 30 min while shaking. Vacuum-filtrate filter plate for 5 seconds.

Add 200 µl blocking buffer (1× Carbo-free Blocking in 1×PBS, VectorLabs) and shake horizontally for 2 min. Vacuum-filtrate filter plate for 5 seconds. Repeat for a total of 4 washing cycles.

Add 200 µl blocking buffer and incubate for 30 min while shaking.

Vacuum-filtrate filter plate for 5 seconds and add 80 µl StabilGuard Choice (SurModics) per well.

Shake horizontally for at least 3 min to resuspend beads. Collect 96× 80 µl in one 15 ml-vial and fill volume up to 11.2 ml. Vortex thoroughly prior further processing (see below).

Immunoassay: In this step, peptide-coupled beads are presented to plasma samples from lung carcinoma patients or plasma samples from healthy donors (multiplexing of n=96 bead regions/peptides per sample).

Add 56 µl assay-buffer (50% StabilZyme Select in PBS, SurModics) into all 96 wells of a new filter plate (Pall).

Add 56 µl of peptide-coupled bead-mix (see above) into all 96 wells.

Vacuum-filtrate filter plate for 5 seconds (beads remain in wells) and add 112.5 µl assay buffer per well.

Add 12.5 µl plasma sample per well (1:4 pre-diluted in 4 mM EDTA, pH 8 and filtrated through a filter plate, Pall) for a final sample dilution of 1:40).

96 samples can therefore be analyzed per plate (96 samples×96 bead regions=9216 data points).

Incubate for 60 min while shaking.

In this step, autoantibodies may bind to an epitope of a peptide coupled to a defined bead region that can later be identified with the Luminex® reader (see below).

Washing step: add 150 µl washing buffer (0.1% Tween 20 in 1×PBS, pH 7.5) and vacuum-filtrate filter plate for 5 seconds. Repeat once for a total of 2 washes.

Immediately prior use, dilute secondary antibody (Leinco, monoclonal mouse IgG2b anti-human IgG [Fc Specific] antibody R-Phycoerythrin, 100 µg/ml) in assay buffer to a final tracer concentration of 3 µg/ml.

Add 100 µl tracer per well and incubate for 60 min while shaking.

In this step tracer bind to the Fc-part of all antibodies that in turn are bound to a peptide-coupled bead. Conjugated R-Phycoerythrin serves as reporter molecule later for fluorescence-measurement with the Luminex® reader (see below).

Washing step: add 150 µl washing buffer (0.1% Tween 20 in 1×PBS, pH 7.5) and vacuum-filtrate filter plate for 5 seconds. Repeat once for a total of 2 washes.

Seal washed plate with an aluminum plate sealer to secure plate from leaking.

Add 150 µl Reading Buffer (1×PBS, pH7.5) in each well. Shake plate for at least 3 min horizontally before measuring to resuspend beads.

Measure plate in a Luminex® reader (e.g. BioPlex200, BioRad) to determine median fluorescence intensities (MFIs) of all 96 bead-regions per well.

In this step a "red" laser will identify the color (="region") of individualized beads (coupled to a known peptide sequence). Simultaneously, a "green" laser will measure MFI (median fluorescence intensity) of the reporter molecule R-Phycoerythrin (coupled to the tracer) bound to the identified bead. Therefore, 96 MFIs are obtained for each well (=each sample).

Data analysis for primary screening: In this step, 96 plasma samples from lung carcinoma patients (LC-samples) and 288 plasma samples from normal donors (ND-samples) are analyzed on all 5735 peptides (=2.2 million data points covering above listed 50 tumor-associated antigens, Table 3). Peptides showing high reactivities in normal samples are excluded, whereas peptides that show low/no reactivity in normal samples but high reactivities in tumor samples are selected for secondary screening.

Reactivities in samples are calculated and evaluated as follows: MFI (median fluorescence intensity) of each peptide (=bead region) divided by median of all peptides (=all bead regions) of respective sample (!). This way, a sample-specific normalization of MFI-values is achieved (quotient). Median of all peptides of one sample (per well) is regarded as the ideal sample-internal reference value because the majority of peptides do not evoke a measurable signal.

Explanation: Background (=peptide-independent signal) varies significantly from sample to sample. 5-10% of samples show peptide-independent high background signals which is normal for immunological assays (e.g. also ELISA). In order to prevent that these signals are regarded as positive, the described sample-internal normalization is highly preferable. This procedure enables high specificities (high background samples from healthy donors are considered as negative).

In publications usually a reference background is determined by analyzing many normal samples and a threshold for all samples is defined by calculation the mean as well as the standard deviation of all obtained signals from all samples. As a consequence, high background samples have a better chance to be regarded as positive although the signal is not related to a specific peptide. This results in a reduced specificity (high background samples from healthy donors are considered as positive).

In short: Normalized value=quotient "Q"=MFI [peptide]/median MFI [all peptides per sample and well]. Two examples are shown below:

Q=1 means that signal from an individual peptide does not differ from median of all peptides (=sample-specific background). Result: No autoantibody is present in respective sample against this peptide.

Q=10 means that signal from an individual peptide is 10-fold higher than median of all peptides (=sample-specific background). Result: Autoantibody is present in respective sample against this peptide (if cut-off <10 was defined. If a cut-off >10 was defined, the signal is considered as negative).

All peptides are selected for secondary screening that show following distribution between the normal cohort (ND) and lung carcinoma cohort (LC) regarding number of reactivities applying various cut-offs (cut-off 6, 8, 10, 12, 14, 20):

LC:ND≥2:0 (at least 2 reactivities in tumor cohort versus 0 reactivities in normal cohort applying respective cut-off);

LC:ND≥3-fold (at least 3 times more reactivities in tumor cohort compared to normal cohort, e.g. 3:1 or 6:2 etc.);

LC:ND=1:0 (only for cut-off 12).

Note: Primary Screening represents a non-stringent selection procedure. Only peptides that cause high reactivities with normal samples compared to lung carcinoma samples are eliminated at this stage.

Data analysis for secondary screening: In this step 240 additional plasma samples from lung carcinoma patients (LC samples) and 720 additional plasma samples from normal donors (ND samples) are analyzed on 754 peptides that were selected during primary screening (approx. 700,000 data points). Peptides showing high reactivities in normal samples are excluded, whereas peptides that show low/no reactivity in normal samples but high reactivities in tumor samples are selected for tertiary screening.

After secondary screening so called hypotheses are generated: Results of the secondary screening are used as "training set" to define conditions that must be validated in a "validation set" during tertiary screening using other normal and tumor samples (in order to simulate a true clinical situation with an IVD where peptide marker and cut-offs are pre-defined).

The following hypotheses are generated:
LC:ND>7-fold (8:0; 8:1; 16:2 etc.);
LC:ND>6-fold (7:0; 7:1; 14:2 etc.);
LC:ND>5-fold (6:0; 6:1; 12:2 etc.);
LC:ND>4-fold (5:0; 5:1; 10:2 etc.);
LC:ND>3-fold (4:0; 4:1; 8:2 etc.).

These 5 conditions are applied using 6 different cut-offs (6, 8, 10, 12, 14, 20) each, resulting in 6×5=30 hypotheses. Examples:

Highest stringency (most peptides are excluded) when LC:ND>7 at lowest cut-off 6 (only those peptides are selected for tertiary screening that show at cut-off 6 at least 8 times more reactivities in tumor cohort (n=240) than in normal cohort (n=720). The obtained peptide set is validated in tertiary screening with new samples applying pre-defined cut-off 6.

Lowest stringency (many peptides are included) when LC:ND>3 at highest cut-off 20 (only those peptides are selected for tertiary screening that show at cut-off 20 at least 4 times more reactivities in tumor cohort (n=240) than in normal cohort (n=720). The obtained peptide set is validated in tertiary screening with new samples applying pre-defined cut-off 20.

Note: The most promising peptides are present in various hypotheses (=defined peptide set at a defined cut-off).

Therefore, after secondary screening 30 different peptide sets are defined consisting of a total of 263 different individual peptides to be validated in tertiary screening ("validation set").

Data analysis for tertiary screening (=cross-validation): In this step a total of 384 plasma samples from lung carcinoma patients (LC-samples) and a total of 2953 plasma samples from normal donors (ND-samples) are analyzed on 263 peptides that represent 30 different hypotheses generated after secondary screening.

Each pre-defined peptide set at a pre-defined cut-off will deliver reactivities in the tumor cohort (defining sensitivity) and in the normal cohort (defining specificity).

The best hypothesis is identified after tertiary screening that confirms the results of the secondary screening and that achieves a specificity of ≥98% at greatest possible sensitivity. This hypothesis was: LC:ND>5-fold (6:0; 6:1; 12:2 etc.) at cut-off 10. This peptide set (listed in Table 4) is selected for the IVD-development of an ELISA-test system.

Additional explanation of this 3-step approach: The described 3-step approach to screen for tumor-associated autoantibodies made it possible to analyze a large number of normal/tumor samples on a large number of peptides (see FIG. 6):

Primary Screening: A large number of peptides and a relatively low number of samples are analyzed to exclude those peptides that are not usable for further screening (high reactivity in normal samples). This saves time and costs.

Secondary Screening: A medium number of peptides (selected in primary screening) and a medium number of samples are analyzed to further exclude peptides and to generate hypotheses ("training set", see above).

Tertiary Screening: A low number of peptides (best candidates building the hypotheses) and a large number of samples warrant that selected peptides are valid in a real clinical screening situation ("validation set") and that no bias occurred due to optimization of a peptide-panel to a measured sample cohort which is relatively small.

Note: During tertiary screening additional samples from other diseases are also tested for "cross-validation" (Asthma, bronchitis, COPD, melanoma, gastric cancer, breast cancer, colon cancer, prostate cancer).

C. ELISA

For validation of Luminex® results and to establish an in vitro diagnostic device for detection of tumor-associated autoantibodies in human blood samples as a screening tool for lung cancer.

Overview: Diluted plasma or serum samples are added to a 96-well immunoplate coated with 21 marker peptides listed in Table 4. If tumor-associated antibodies are present in the sample, they will bind to a peptide and can be detected via a secondary anti-human IgG (Fc)-antibody conjugated with horseradish peroxidase HRP (visualized by HRP-substrate TMB in a colorimetric assay).

Coating of plate: N-terminal biotinylated peptides are added to Streptavidin-coated microtiter plate, 96-well (Nunc Immobilizer). In detail:

Before coating prepare plates by washing 3× with 250 μl/well of PBST-buffer (0.05% Tween 20 in 1×PBS, pH7.2).

High-purity peptides (1 μg/μl in max. 20% DMSO) are used as starting material.

3 or 4 peptides (see layout in FIG. 7) are mixed together in PBST-buffer to obtain 500 pg/μl (each peptide has a final coating concentration of 167 pg/μl or 125 pg/μl, respectively, in coating-solution PBST).

Add 80 μl of peptide mixes 1-6 (layout of plate see below, one peptide mix per row).

For row G and H, no peptide is coated. Instead, 80 μl of a Biotin-solution (4.8 μg/ml D-Biotin in PBST) is added to the wells. These wells will be used for normalization (determination of background per sample).

Incubate for 1 h at room temperature for coating.

Wash 3 times with 3× 250 μl PBST-buffer and add 200 μl blocking solution (1% BSA, 0.1% Tween20 in PBS, pH 7.5).

Incubate for 1 h at room temperature for blocking.

Invert plate/remove blocking solution and place at 25° C. for 1 h (until dry). Store in aluminum foil with desiccant at 4° C.

Immunoassay: Diluted plasma or serum samples are added in one column of peptide-coated plate in order to detect autoantibodies that bind to one or more of peptide mixes 1-6 (row A-F, see layout in FIG. 7). Wells in row G and H are used for sample-internal normalization (see below). Therefore, a total of 12 samples can be analyzed per plate (if no replicates are measured). In detail:

Dilute serum or plasma sample 1:400 in assay-buffer (50% StabilZyme Select, SurModics and 50% Low-Cross Buffer, Candor) and add to one column of immunoplate (one sample per column).

Incubate at RT for 1 h (shake at 500 rpm).

Wash 3 times with 3× 350 μl PBST-buffer.

Add 100 μl secondary antibody

Polyclonal goat anti-human IgG (Fc-specific), conjugated with horseradish peroxidase HRP, Dianova;

Final concentration: 0.04 μg/μl in 50% StabilZymeHRP, SurModics and 50% LowCross Buffer, Candor.

Incubate at RT for 1 h (shake at 500 rpm).

Wash 3 times with 3× 350 μl PBST-buffer.

Dispense 100 μl TMB-substrate per well. Incubate at RT for 15 min.

Stop reaction by adding 100 μl stop solution (dilute 25% sulfuric acid 1:10 in $H_2O$=2.5% sulfuric acid).

Measure in ELISA-reader at 450/620 nm.

Data analysis and evaluation of results: In this step, samples are defined as "negative" (no tumor-associated autoantibodies detectable meaning that no tumor was found) or "positive" (tumor-associated autoantibodies are detected meaning that a tumor is present and further diagnostics like imaging techniques CT or MRT are required to localize it). Reactivities in samples are calculated and evaluated as follows:

OD (optical density) at 620 nm is subtracted from OD at 450 nm for each well: [OD450-620 nm].

Sample 1 in column 1 of immunoplate (see layout in FIG. 7):

Marker 1 (Peptide-Mix 1): [OD450-620 nm] of well A1 is divided by mean of [OD450-620 nm] of wells G1 and H1 (blank normalization).=Quotient 1;

Marker 2 (Peptide-Mix 2): [OD450-620 nm] of well A2 is divided by mean of [OD450-620 nm] of well G1 and H1 (blank normalization).=Quotient 2;

Same procedure for markers 3-6 (peptide-mixes 3-6)= Quotients 3-6.

Samples 2-12 in columns 2-12 of immunoplate, respectively, are calculated the same way meaning that for each sample quotients 1-6 are calculated.

Note: This sample-internal blank normalization is preferable because background (signals obtained from wells where no peptide is coated, rows G and H) varies from sample to sample. Refer also to explanations of primary screening described above.

Test result: If any quotient 1-6 of a sample exceeds a defined cut-off, the sample is defined as "positive". If all 6 quotients of a sample are below the defined cut-off, the sample is defined as "negative".

Performance data: The performance characteristics of the lung cancer screening test are dependent on the envisaged target screening population (age-group of smokers, see FIG. 8). Smokers that are older than 70 years reveal a higher prevalence for lung cancer than for example smokers that are older than 50 years. The prevalence of the disease in the chosen subpopulation in turn influence the PPV (positive predictive value). In addition, lowering the cut-off for the ELISA screening test leads to more reactivities in the lung cancer group (results in a higher sensitivity) but also to more reactivities in the healthy donor group (results in a higher false-positive rate and therefore a lower PPV).

REFERENCES

[1] Zaenker P, Ziman M R. Serologic autoantibodies as diagnostic cancer biomarkers—a review. Cancer Epidemiol Biomarkers Prev. 2013 December; 22(12):2161-81.

[2] Brower V. Biomarker studies abound for early detection of lung cancer. J Natl Cancer Inst. 2009; 101:11-3.
[3] Zhang C, Ye L, Guan S, Jin S, Wang W, Sun S, Lee K H, Wei J, Liu B. Autoantibodies against p16 protein-derived peptides may be a potential biomarker for non-small cell lung cancer. Tumour Biol. 2013 Oct. 13.
[4] Solassol J, Harmand P O, Maudelonde T, Pujol J L. Autoantibodies against tumor-related antigens: new tools for early detection of lung cancer. Bull Cancer 2011 December; 98(12):1419-30.
[5] Cuzick J, Szarewski A, Cubie H, et al. Management of women who test positive for high-risk types of human papillomavirus: the HART study. Lancet. Dec. 6, 2003; 362(9399):1871-1876.
[6] Harper D M. Predictive Values: What Do They Tell Us? Trends in Cervical Health. www.cervicalhealth.com. Vol. 4; Winter 2007.
[7] The National Lung Screening Trial Research Team. Reduced Lung-Cancer Mortality with Low-Dose Computed Tomographic Screening. N Engl J Med 2011; 365:395-409 Aug. 4, 2011.
[8] Goulart B H, Bensink M E, Mummy D G, Ramsey S D. Lung cancer screening with low-dose computed tomography: costs, national expenditures, and cost-effectiveness. J Natl Compr Canc Netw. 2012 February; 10(2): 267-75.
[9] Pereira-Faca S R, Kuick R, Purays E, Zhang Q, Krasnoselsky A L, Phanstiel D, et al. Identification of 14-3-3 theta as an antigen that induces a humoral response in lung cancer. Cancer Res. 2007; 67:12000-6.
[10] Qiu J, Choi G, Li L, Wang H, Pitteri S J, Pereira-Faca S R, et al. Occurrence of autoantibodies to annexin I, 14-3-3 theta and LAMR1 in prediagnostic lung cancer sera. J Clin Oncol. 2008; 26:5060-6.
[11] Yang F, Xiao Z Q, Zhang X Z, Li C, Zhang P F, Chen M Y, et al. Identification of tumor antigens in human lung squamous carcinoma by serological proteome analysis. J Proteome Res. 2007; 6:751-8.
[12] Chapman C J, Murray A, McElveen J E, Sahin U, Luxemburger U, Türeci O, et al. Autoantibodies in lung cancer: possibilities for early detection and subsequent cure. Thorax. 2008; 63:228-33.
[13] Chapman C J, Healey G F, Murray A, Boyle P, Robertson C, Peek L J, Allen J, Thorpe A J, Hamilton-Fairley G, Parsy-Kowalska C B, MacDonald I K, Jewell W, Maddison P, Robertson J F. EarlyCDT®-Lung test: improved clinical utility through additional autoantibody assays. Tumour Biol. 2012 October; 33(5):1319-26.
[14] Shan Q, Lou X, Xiao T, Zhang J, Sun H, Gao Y, Cheng S, Wu L, Xu N, Liu S. A cancer/testis antigen microarray to screen autoantibody biomarkers of non-small cell lung cancer. Cancer Lett. 2013 Jan. 1; 328(1):160-7.

The invention claimed is:

1. A method for the diagnosis, prognosis and/or monitoring of and treating lung cancer in a patient, the method comprising detecting and/or determining the amount of autoantibodies in a biological sample isolated from the patient that specifically bind isolated peptides on a panel, wherein the panel of isolated peptides comprises at least one isolated peptide for each of SEQ ID NOs: 1 to 21, wherein the isolated peptides consist of 12 to 25 amino acid residues and comprise at least 12 contiguous amino acids for each of SEQ ID NOs: 1 to 21; and treating the lung cancer in the patient, wherein the treatment comprises administering surgery, chemotherapy, hormonal therapy, radiation therapy, or immunotherapy/targeted therapy to the patient.

2. The method according to claim 1, wherein the isolated peptides on the panel comprise one or more isolated peptides selected from the group consisting of SEQ ID NOs: 1 to 21.

3. The method according to claim 1, wherein the presence of the autoantibodies indicates the presence of lung cancer or an increased risk of developing lung cancer.

4. The method according to claim 1, wherein the detection and/or determination of the amount of autoantibodies takes place with an immunoassay.

5. The method according to claim 1, wherein the detection and/or determination of the amount of the autoantibodies comprises:
  (i) contacting the biological sample with the isolated peptides on the panel as defined in claim 1, and
  (ii) detecting the formation of complexes between the plurality of isolated peptides and the autoantibodies.

6. The method according to claim 5, wherein the plurality of isolated peptides are immobilized on a support.

7. The method according to claim 1, wherein the biological sample comprises body fluid and/or body tissue.

8. The method according to claim 7, wherein the body fluid is blood serum or blood plasma.

9. The method according to claim 1, wherein the cancer is early stage lung cancer.

10. The method according to claim 1, wherein the isolated peptides on the panel comprise each of SEQ ID NOs: 1 to 21.

11. The method according to claim 1, wherein the method facilitates a specificity of at least 97.5% and a sensitivity of at least 23%.

12. The method according to claim 1, wherein the isolated peptides are modified so as to allow immobilization on a support.

13. The method according to claim 12, wherein the isolated peptides comprise additional amino acid residues or tags that facilitate direct or indirect binding to the support material.

14. A method of detecting and/or determining the amount of autoantibodies specifically binding to a panel of isolated peptides in a biological sample isolated from a patient and treating the patient, the method comprising: obtaining a biological sample from a patient and detecting and/or determining the amount of autoantibodies that specifically bind isolated peptides on the panel by contacting the biological sample with the isolated peptides on the panel, wherein the panel of isolated peptides comprises at least one isolated peptide for each of SEQ ID NOs: 1 to 21, wherein the isolated peptides consist of 12 to 25 amino acid residues and comprise at least 12 contiguous amino acid residues for each of SEQ ID NOs: 1 to 21 and detecting and/or determining the amount of autoantibodies specifically binding to the panel of isolated peptides; and treating the patient, wherein the treatment comprises administering surgery, chemotherapy, hormonal therapy, radiation therapy, or immunotherapy/targeted therapy to the patient.

15. The method according to claim 14, wherein the isolated peptides on the panel comprise one or more isolated peptides selected from the group consisting of SEQ ID NOs: 1 to 21.

16. The method according to claim 14, wherein the presence of the autoantibodies indicates the presence of lung cancer or an increased risk of developing lung cancer.

17. The method according to claim 14, wherein the detection and/or determination of the amount of autoantibodies takes place with an immunoassay.

18. The method according to claim 14, wherein the detection and/or determination of the amount of the autoantibodies comprises:
  (i) contacting the biological sample with the isolated peptides on the panel as defined in claim 14, and
  (ii) detecting the formation of complexes between the plurality of isolated peptides and the autoantibodies.

19. The method according to claim 18, wherein the plurality of isolated peptides are immobilized on a support.

20. The method according to claim 14, wherein the biological sample comprises body fluid and/or body tissue.

21. The method according to claim 20, wherein the body fluid is blood serum or blood plasma.

22. The method according to claim 14, wherein the cancer is early stage lung cancer.

23. The method according to claim 14, wherein the isolated peptides on the panel comprise each of SEQ ID NOs: 1 to 21.

24. The method according to claim 14, wherein the method facilitates a specificity of at least 97.5% and a sensitivity of at least 23%.

25. The method according to claim 14, wherein the isolated peptides are modified so as to allow immobilization on a support.

26. The method according to claim 25, wherein the isolated peptides comprise additional amino acid residues or tags that facilitate direct or indirect binding to the support material.

* * * * *